United States Patent
Marty et al.

(10) Patent No.: US 11,549,105 B2
(45) Date of Patent: Jan. 10, 2023

(54) PROTEASES AND USES THEREOF

(71) Applicant: CARBIOS, Saint-Beauzire (FR)

(72) Inventors: Alain Marty, Toulouse (FR); Sophie Duquesne, Toulouse (FR); Marie Guicherd, Toulouse (FR); Marc Gueroult, Reims (FR); Isabelle Andre, Toulouse (FR)

(73) Assignee: CARBIOS, Saint-Beauzire (FR)

( * ) Notice: Subject to any disclaimer, the term of this patent is extended or adjusted under 35 U.S.C. 154(b) by 0 days.

(21) Appl. No.: 16/955,088

(22) PCT Filed: Dec. 21, 2018

(86) PCT No.: PCT/EP2018/086526
§ 371 (c)(1),
(2) Date: Jun. 18, 2020

(87) PCT Pub. No.: WO2019/122308
PCT Pub. Date: Jun. 27, 2019

(65) Prior Publication Data
US 2020/0385698 A1   Dec. 10, 2020

(30) Foreign Application Priority Data
Dec. 21, 2017 (EP) ..................... 17306878

(51) Int. Cl.
*C12N 9/52* (2006.01)
(52) U.S. Cl.
CPC ..................... *C12N 9/52* (2013.01)
(58) Field of Classification Search
CPC ............. C12N 9/52; C12N 9/18; C12N 9/16
See application file for complete search history.

(56) References Cited

U.S. PATENT DOCUMENTS

| | | | |
|---|---|---|---|
| 10,124,512 B2 | 11/2018 | Boisart et al. | |
| 10,287,561 B2 | 5/2019 | Alvarez et al. | |
| 10,385,183 B2 | 8/2019 | Maille | |
| 10,508,269 B2 | 12/2019 | Li et al. | |
| 10,584,320 B2 | 3/2020 | Topham et al. | |
| 10,590,401 B2 | 3/2020 | Tournier et al. | |
| 10,626,242 B2 | 4/2020 | Ferreira et al. | |
| 10,717,996 B2 | 7/2020 | Dusseaux et al. | |
| 10,723,848 B2 | 7/2020 | Chateau et al. | |
| 10,767,026 B2 | 9/2020 | Desrousseaux et al. | |
| 10,829,754 B2 | 11/2020 | Marty et al. | |
| 11,072,784 B2 | 7/2021 | Tournier et al. | |
| 2018/0142097 A1 | 5/2018 | Guemard et al. | |
| 2020/0190279 A1 | 6/2020 | Guemard et al. | |
| 2020/0339766 A1 | 10/2020 | Chateau et al. | |
| 2020/0392303 A1 | 12/2020 | Desrousseaux et al. | |
| 2021/0009980 A1 | 1/2021 | Marty et al. | |
| 2021/0163906 A1 | 6/2021 | David et al. | |
| 2021/0171921 A1 | 6/2021 | Andre et al. | |
| 2021/0180037 A1 | 6/2021 | Duquesne et al. | |
| 2021/0261931 A9 | 8/2021 | Topham et al. | |

FOREIGN PATENT DOCUMENTS

| | | |
|---|---|---|
| JP | 2016 036327 | 3/2016 |
| WO | WO 2014/122698 | 8/2014 |
| WO | WO 2016/062695 | 4/2016 |

OTHER PUBLICATIONS

Witkowski et al., Biochemistry 38:11643-11650, 1999.*
Tang et al., Phil Trans R Soc B 368:Mar. 18, 2012, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Guo et al., PNAS 101(25):9205-9210, 2004.*
Written Opinion in International Application No. PCT/EP2018/086526, dated Mar. 11, 2019, pp. 1-7.
Claims as filed for U.S. Appl. No. 17/291,290, filed May 5, 2021, pp. 1-4.
Claims as filed for U.S. Appl. No. 17/291,291, filed May 5, 2021, pp. 1-3.

* cited by examiner

*Primary Examiner* — Delia M Ramirez
(74) *Attorney, Agent, or Firm* — Saliwanchik, Lloyd & Eisenschenk

(57) ABSTRACT

The present invention relates to novel proteases, more particularly to protease variants having improved activity compared to the protease of SEQ ID NO: 1 and the uses thereof for degrading polyester containing material, such as plastic products. The proteases of the invention are particularly suited to degrade polylactic acid, and material containing polylactic acid.

Figure 1A:
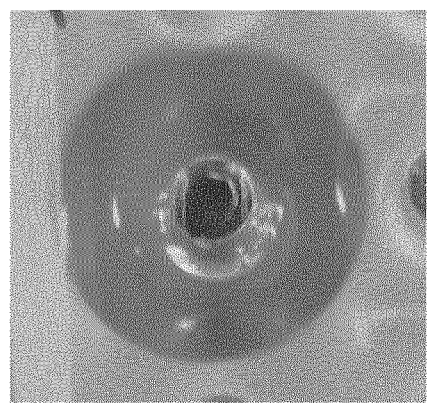

16 Claims, 1 Drawing Sheet
Specification includes a Sequence Listing.

PROTEASES AND USES THEREOF

CROSS-REFERENCE TO RELATED APPLICATION

This application is the U.S. national stage application of International Patent Application No. PCT/EP2018/086526, filed Dec. 21, 2018.

The Sequence Listing for this application is labeled "Seq-List.txt" which was created on May 29, 2020 and is 16 KB. The entire content of the sequence listing is incorporated herein by reference in its entirety.

The present invention relates to novel proteases, more particularly to proteases having improved activity compared to a parent protease and the uses thereof for degrading polyester or polyester containing material, such as plastic products. The proteases of the invention are particularly suited to degrade polylactic acid, and polylactic acid containing material.

BACKGROUND

Proteases are able to catalyze the hydrolysis of a variety of polymers, including polyesters. In this context, proteases have shown promising effects in a number of industrial applications, including as detergents for dishwashing and laundry applications, as degrading enzymes for processing biomass and food, as biocatalysts in the detoxification of environmental pollutants or for the treatment of polyester fabrics in the textile industry. Likewise, the use of proteases as degrading enzymes for hydrolyzing polylactic acid (PLA) is of particular interest. Indeed, PLA is a bio-based polymer (i.e., a polymer derived from natural and/or renewable sources) that is used in a large number of technical fields, such as flexible and rigid packaging, bags, mulching films, as well as in the manufacture of clothes and carpets. Accordingly, PLA accumulation in landfills becomes an increasing ecological problem.

Among proteases, serine proteases (EC 3.4.21) are enzymes that cleave peptide amide bonds in proteins, in which serine serves as the nucleophilic amino acid in the enzyme active site. Serine proteases are found ubiquitously in both eukaryotes and prokaryotes. Numerous bacterial serine proteases have been identified initially in *Bacillus* and more recently in other mesophilic hosts. However, an increasing number of serine proteases have been isolated from thermophilic and hyperthermophilic bacteria.

Biological degradation, and more particularly enzymatic degradation, is considered as an interesting solution to decrease plastic waste accumulation. Indeed, enzymes are able to accelerate hydrolysis of polyester containing material, and more particularly of plastic products, even down to the monomer level. Furthermore, the hydrolysate (i.e., monomers and oligomers) can be recycled as material for the synthesis of new polymers. Recently, new plastic materials have been developed that integrate biological entities suitable for degrading at least one polymer of the plastic material, leading to the production of biodegradable plastic products. As an example, plastic products made of PLA and including proteases have been produced. Such biodegradable plastics may at least partially solve the problem of plastic build-up in landfill sites and natural habitats.

In this context, several proteases have been identified as candidate degrading enzymes. For instance, a protease of *Actinomadura* sp. (WO 2016/062695) has been described for its capacity to degrade polyester, and more particularly polylactic acid.

However, there is still a need for proteases with improved activity to allow a degrading process with higher efficiency, and thereby enhancing the competitiveness of biodegradable plastic production processes, biological polyester degrading processes and/or biological recycling processes.

SUMMARY OF THE INVENTION

The present invention provides new variants of proteases exhibiting increased polyester degrading activity compared to a parent, or wild-type protease. These proteases are particularly useful in processes for degrading polyester(s) and/or plastic material and product containing polyester(s), such as PLA or plastic material and product containing polylactic acid (PLA). More particularly, the present invention provides variants of a protease of *Actinomadura* sp. having the amino acid sequence as set forth in SEQ ID No 1, referenced herein as the parent protease or wild-type protease. Interestingly, both the wild-type protease and the variants are considered as subtilisin-like proteases. The present invention further provides process for degrading polyester(s) and/or plastic material and product containing polyester(s), and more particularly polylactic acid (PLA) and/or plastic material and product containing PLA, using a variant of the invention.

In this regard, it is an object of the invention to provide a protease variant which (i) has at least 90%, 95%, 96%, 97%, 98% or 99% identity to the full length amino acid sequence set forth in SEQ ID No 1, and (ii) has at least one amino acid substitution at a position selected from S101, S103, T106, G131, or G133, wherein the positions are numbered by reference to the amino acid sequence set forth in SEQ ID No 1, and (iii) exhibits increased polyester degrading activity compared to the protease of SEQ ID No 1.

In a particular embodiment, the protease comprises at least one substitution selected from the group consisting of S101F/L/M/W/Y, S103L, T106I/L, G131I, or G133K, preferably at least one substitution selected from S101F/L/M/W/Y, more preferably at least the substitution S101F.

It is a further object of the invention to provide a protease variant which (i) has at least 75%, 80%, 85%, 90%, 95%, 96%, 97%, 98% or 99% identity to the full length amino acid sequence set forth in SEQ ID No 1, and (ii) has at least one amino acid substitution at a position selected from S101F/L/M/W/Y, S103L, T106I/L, G131I, or G133K, wherein the positions are numbered by reference to the amino acid sequence set forth in SEQ ID No 1, preferably at least a substitution selected from S101F/L/M/W/Y, more preferably at least the substitution S101F and (iii) exhibits increased polyester degrading activity compared to the protease of SEQ ID No 1.

It is another object of the invention to provide a protease which (i) has at least 75%, 80%, 85%, 90%, 95%, 96%, 97%, 98% or 99% identity to the full length amino acid sequence set forth in SEQ ID No 1, and (ii) has at least an amino acid substitution at both positions S101 and S103, wherein the positions are numbered by reference to the amino acid sequence set forth in SEQ ID No 1, and (iii) exhibits increased polyester degrading activity compared to the protease of SEQ ID No 1. In such case, the substitutions are preferably selected from S101F/L/M/W/Y and S103L.

The invention more particularly provides specific proteases having at least 75%, 80%, 85%, 90%, 95%, 96%, 97%, 98% or 99% identity to the full length amino acid sequence set forth in SEQ ID No 1, and at least a combination of substitutions selected from S101F+S103L, S101F+

T106I, T106I+G133K, S101F+S103L+T106I, S101F+ S103L+G133K, S101F+T106I+G133K, S101F+S103L+ T106L, S101F+S103L+T106I+G133K, S101F+S103L+ T106I+G131I, preferably S101F+S103L+T106I/L.

It is another object of the invention to provide a nucleic acid encoding a protease as defined above. The present invention also relates to an expression cassette or an expression vector comprising said nucleic acid, and to a host cell comprising said nucleic acid, expression cassette or vector.

It is a further object of the invention to provide a method of producing a protease as defined above comprising:

(a) culturing a host cell as defined above under conditions suitable to express a nucleic acid encoding a protease; and optionally (b) recovering said protease from the cell culture.

The present invention also relates to a method of degrading a plastic product containing at least one polyester, preferably PLA, comprising (a) contacting the plastic product with a protease or host cell as defined above, thereby degrading the plastic product; and optionally (b) recovering monomers and/or oligomers, preferably monomers and/or oligomers of lactic acid (LA).

The present invention also relates to a polyester containing material comprising a protease or host cell according to the invention. The present invention relates more preferably to a polylactic acid (PLA) containing material comprising a protease or host cell or composition according to the invention. The invention also provides a process for producing such polyester containing material comprising a step of mixing a polyester, preferably PLA, and a protease or host cell or composition according to the invention, wherein the mixing step is performed at a temperature at which the polyester is in a partially or totally molten state, preferably during an extrusion process.

The present invention further relates to the use of a protease as described above for degrading a polyester containing material, more preferably a PLA containing material.

LEGEND TO THE FIGURES

Figure 1B:
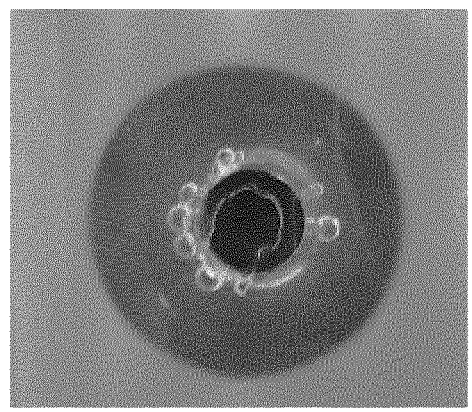
Figure 1C:
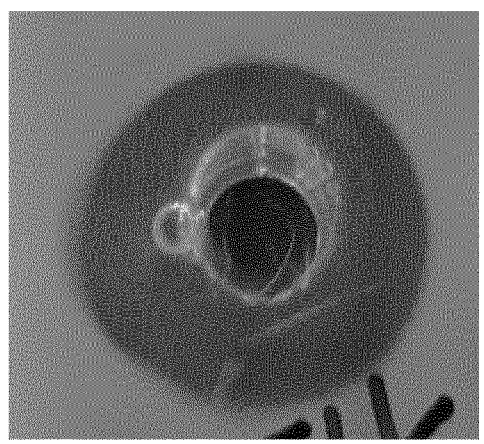

FIGS. 1A&1B&1C show specific protease activity based upon the degradation of milk protein under solid form for both wild-type protease (SEQ ID No 1—FIG. 1A) and proteases of the invention (V8—FIGS. 1B and V19—FIG. 1C) after 5 hours incubation at 45° C.

DETAILED DESCRIPTION OF THE INVENTION

Definitions

The present disclosure will be best understood by reference to the following definitions.

Herein, the terms "peptide", "polypeptide", "protein", "enzyme" refer to a chain of amino acids linked by peptide bonds, regardless of the number of amino acids forming said chain. The amino acids are herein represented by their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr).

The term "protease" refers to an enzyme which belongs to a class of hydrolases classified as EC 3.4 according to Enzyme Nomenclature that is able to catalyze the hydrolysis of a peptide bond in a peptide or a protein. The term "serine protease" refers to proteases classified as EC 3.4.21 according to the nomenclature of the Enzyme Commission.

The terms "wild-type protein" or "parent protein" are used interchangeably and refer to the non-mutated version of a polypeptide as it appears naturally. An example of a parent protease is a protease having the amino acid sequence as set forth in SEQ ID No 1.

The terms "mutant" and "variant" may be used interchangeably to refer to polypeptides derived from a wild-type or parent polypeptide and comprising at least one modification or alteration, i.e., a substitution, insertion, and/or deletion, at one or more positions. Variants may be obtained by various techniques well known in the art. In particular, examples of techniques for altering a DNA sequence encoding the wild-type protein, include, but are not limited to, site-directed mutagenesis, random mutagenesis and synthetic oligonucleotide construction. Thus, the terms "modification" and "alteration" as used herein, in relation to a particular position, means that at least the amino acid in this particular position has been modified compared to the amino acid in this particular position in the wild-type protein.

A "substitution" means that an amino acid residue is replaced by another amino acid residue. Preferably, the term "substitution" refers to the replacement of an amino acid residue by another selected from the naturally-occurring standard 20 amino acid residues, rare naturally occurring amino acid residues (e.g. hydroxyproline, hydroxylysine, allohydroxylysine, 6-N-methylysine, N-ethylglycine, N-methylglycine, N-ethylasparagine, allo-isoleucine, N-methylisoleucine, N-methylvaline, pyroglutamine, aminobutyric acid, ornithine, norleucine, norvaline), and non-naturally occurring amino acid residue, often made synthetically, (e.g. cyclohexyl-alanine). Preferably, the term "substitution" refers to the replacement of an amino acid residue by another selected from the naturally-occurring standard 20 amino acid residues (G, P, A, V, L, I, M, C, F, Y, W, H, K, R, Q, N, E, D, S and T). The sign "+" indicates a combination of substitutions. In the present document, the following terminology is used to designate a substitution: Y167R denotes that amino acid residue Tyrosine (Y) at position 167 of a parent sequence is substituted by an Arginine (R). Y167V/I/M denotes that amino acid residue Tyrosine (Y) at position 167 of a parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

Unless otherwise specified, the positions disclosed in the present application are numbered by reference to the amino acid sequence set forth in SEQ ID No 1.

As used herein, the term "sequence identity" or "identity" refers to the number (or fraction expressed as a percentage %) of matches (identical amino acid residues) between two polypeptide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithm (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as blast.ncbi.nlm.nih.gov/ or Worldwide Website: ebi.ac.uk/Tools/emboss/). Those skilled in the art can determine appropriate parameters for measuring alignment, including any algorithms needed to achieve maximal alignment over the full length of the sequences being compared. For purposes herein, % amino acid sequence identity values refers to values generated using the pair wise sequence alignment program EMBOSS Needle that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

The term "recombinant" refers to a nucleic acid construct, a vector, a polypeptide or a cell produced by genetic engineering.

The term "expression", as used herein, refers to any step involved in the production of a polypeptide such as transcription, post-transcriptional modification, translation, post-translational modification, or secretion.

According to the invention, "oligomers" refer to molecules containing from 2 to about 20 monomers.

In the present description, "polyesters" encompass polylactic acid (PLA), polyethylene terephthalate (PET), polytrimethylene terephthalate (PTT), polybutylene terephthalate (PBT), polyethylene isosorbide terephthalate (PEIT), polyhydroxyalkanoate (PHA), polybutylene succinate (PBS), polybutylene succinate adipate (PBSA), polybutylene adipate terephthalate (PBAT), polyethylene furanoate (PEF), polycaprolactone (PCL), or poly(ethylene adipate) (PEA), as well as any blends/mixtures of these polymers. In a particular embodiment, "polyester" also encompasses poly(glycolic acid) (PGA) or poly(lactic-co-glycolic acid) (PLGA) as well as any blends/mixtures of these polymers.

In the context of the invention, a "polyester containing material" or "polyester containing product" refers to a product, such as plastic product, comprising at least one polyester in crystalline, semi-crystalline or totally amorphous form. In a particular embodiment, the polyester containing material refers to any item made from at least one plastic material, such as plastic sheet, tube, rod, profile, shape, film, massive block, fiber, textiles, etc., which contains at least one polyester, and possibly other substances or additives, such as plasticizers, mineral or organic fillers. In another particular embodiment, the polyester containing material refers to textile, fabrics or fibers comprising at least one polyester. In another particular embodiment, the polyester containing material refers to plastic waste or fiber waste comprising at least one polyester. In another particular embodiment, the polyester containing material refers to a plastic compound, or plastic formulation, in a molten or solid state, suitable for making a plastic product.

Within the context of the invention, the term "increased degrading activity" indicates an increased ability of the enzyme to degrade a polyester, preferably PLA or a plastic product or material, comprising at least a polyester, preferably at least PLA, as compared to the protease of SEQ ID No 1. Such an increase is typically of about 5%, 10%, 20%, 30%, 40%, 50%, 100%, 200%, 300%, 400%, 500% or more in comparison to the parent protease.

The activity of a protein may be evaluated by the one skilled in the art, according to methods known per se in the art. For instance, the activity can be assessed by the measurement of the specific protease activity rate, the measurement of the hydrolysis of pNA (N-succinyl-Ala-Ala-Ala-p-nitroanilide), the measurement of the specific polyester's depolymerization activity rate, the measurement of the rate to degrade a solid polyester compound or protein dispersed in an agar plate, the measurement of the decrease of the turbidity of an emulsion containing a polyester, or the measurement of the specific polyester's depolymerization activity rate in reactor.

Within the context of the invention, the term "specific degrading activity" for a targeted polyester designates the initial rate of monomers and/or oligomers, in mg, released per hour and per mg of enzyme under suitable conditions of temperature, pH and buffer, when contacting a plastic product containing said targeted polyester with a protease according to the invention. As an example, the specific degrading activity for PLA corresponds to the mg of lactic acid and dimers of lactic acid produced per hour and per mg of enzyme, or to the µmol of PLA hydrolyzed/min and per mg of enzyme, as determined in the linear part of the hydrolysis curve.

Novel Proteases

By working on development of novel proteases having improved polyester-degrading activity as compared to enzymes currently available, the inventors have further worked on the serine protease having the amino acid sequence of SEQ ID No 1 and have been able to develop variants thereof that exhibit improved polyester-degrading activity. In particular, the inventors have identified specific amino acid residues within the protein, which are intended to be in contact with a polyester substrate and which may be advantageously modified to promote the contact of the polyester substrate with the protein. Without being bound by theory, it is believed such modifications increase adsorption of the protease on the polyester resulting in an improved degrading activity. The inventors have thus been able to develop novel proteases derived from SEQ ID No 1 that show higher activity and are particularly suited to degrade polyester or polyester-containing products. Interestingly, these new proteases have superior properties for use in industrial processes. The proteases newly developed exhibit an improved activity in conditions at which industrial production of degradable plastic products can be performed and/or environmental degradation of plastic products can be obtained.

According to an embodiment, the protease is a variant of the protease of SEQ ID No 1, which has at least 90%, 95%, 96%, 97%, 98% or 99% identity to the full length amino acid sequence set forth in SEQ ID No 1, and which has at least one substitution at a position selected from S101, S103, T106, G131 or G133, wherein the positions are numbered by reference to the amino acid sequence set forth in SEQ ID No 1.

The targeted amino acid(s) may potentially be replaced by any amino acid selected from naturally-occurring amino acid residues, rare naturally occurring amino acid residues and non-naturally occurring amino acid residues, as long as the resulting polypeptide retains protease activity. Preferably, the targeted amino acid(s) may be replaced by any one of the 19 other amino acids.

Alternatively or in addition, the protease of the invention (i) has at least 75%, 80%, 85%, 90%, 95%, 96%, 97%, 98% or 99% identity to the full length amino acid sequence set forth in SEQ ID No 1, and (ii) has at least one amino acid substitution at a position selected from S101F/L/M/W/Y, S103L, T106I/L, G131I, or G133K, wherein the positions are numbered by reference to the amino acid sequence set forth in SEQ ID No 1, preferably at least a substitution selected from S101F/L/M/W/Y, more preferably at least the substitution S101F and (iii) exhibits increased polyester degrading activity compared to the protease of SEQ ID No 1. All following limitations may apply to both embodiments.

In a particular embodiment, the protease variant comprises a single substitution as compared to SEQ ID No 1, at a position selected from S101, S103, T106, G131 or G133, preferably at position S101 or S103. Preferably, the protease variant comprises a single substitution selected from S101F/L/M/W/Y, S103L, T106I/L, G131I or G133K, more preferably selected from S101F or S103L.

In a particular embodiment, the protease has the amino acid sequence as set forth in SEQ ID No 1, except the substitution S101F (V1), S103L (V2), T106I (V3), G131I (V4), G133K (V5), S101L (V14), S101M (V15), S101W (V16), S101Y (V17) or T106L (V18).

In another particular embodiment, the protease variant comprises two or more substitutions as compared to SEQ ID No 1, wherein at least one substitution is at a position selected from S101, S103, T106, G131 or G133. In a preferred embodiment, the variant comprises at least one substitution at position S101, S103 or T106. In a particular embodiment, the protease variant comprises a least one substitution selected from S101F/L/M/W/Y, S103L, T106I/L, G131I or G133K. Preferably, the protease variant comprises at least the substitution S101F, S103L or T106I/L.

In another particular embodiment, the protease variant comprises at least two substitutions at positions selected from S101, S103, T106, G131 or G133. Advantageously, the protease variant comprises at least two substitutions selected from S101F/L/M/W/Y, S103L, T106I/L, G131I or G133K.

Alternatively, or in addition, the protease of the invention (i) has at least 75%, 80%, 85%, 90%, 95%, 96%, 97%, 98% or 99% identity to the full length amino acid sequence set forth in SEQ ID No 1, and (ii) has at least an amino acid substitution at both positions S101 and S103, wherein the positions are numbered by reference to the amino acid sequence set forth in SEQ ID No1, and (iii) exhibits increased polyester degrading activity compared to the protease of SEQ ID No 1. Advantageously the substitutions are selected from S101F/L/M/W/Y and S103L, preferably consist of S101F and S103L.

In a particular embodiment, the protease has the amino acid sequence as set forth in SEQ ID No 1, except a combination of substitutions selected from S101F/L/M/W/Y+S103L.

Alternatively, or in addition, the protease of the invention (i) has at least 75%, 80%, 85%, 90%, 95%, 96%, 97%, 98% or 99% identity to the full length amino acid sequence set forth in SEQ ID No 1, and (ii) has at least an amino acid substitution at both positions S103 and T106, wherein the positions are numbered by reference to the amino acid sequence set forth in SEQ ID No 1, and (iii) exhibits increased polyester degrading activity compared to the protease of SEQ ID No 1. Advantageously the substitutions are selected from S103L and T106I/L.

Alternatively, or in addition, the protease of the invention (i) has at least 85%, 90%, 95%, 96%, 97%, 98% or 99% identity to the full length amino acid sequence set forth in SEQ ID No 1, and (ii) has at least an amino acid substitution at both positions S101 and T106, wherein the positions are numbered by reference to the amino acid sequence set forth in SEQ ID No 1, and (iii) exhibits increased polyester degrading activity compared to the protease of SEQ ID No 1. Advantageously the substitutions are selected from S101F/L/M/W/Y and T106I/L, preferably consist of S101F and T106I/L.

Alternatively, or in addition, the protease of the invention (i) has at least 75%, 80%, 85%, 90%, 95%, 96%, 97%, 98% or 99% identity to the full length amino acid sequence set forth in SEQ ID No 1, and (ii) has at least an amino acid substitution at both positions T106 and G133, wherein the positions are numbered by reference to the amino acid sequence set forth in SEQ ID No 1, and (iii) exhibits increased polyester degrading activity compared to the protease of SEQ ID No 1. Advantageously the substitutions are selected from T106I/L and G133K.

In a particular embodiment, the protease comprises at least two substitutions selected from S101F+S103L, S101F+T106I, T106I+G133K, preferably at least the combination S101F+S103L.

In a particular embodiment, the protease has the amino acid sequence as set forth in SEQ ID No 1, except a combination of substitution selected from S101F+S103L (V6), S101F+T106I (V7), S103L+T106L, and T106I+G133K (V9), preferably the combination S101F+S103L.

In a particular embodiment, the protease comprises at least three substitutions at positions selected from S101, S103, T106, G131 or G133. Advantageously, the protease variant comprises at least three substitutions selected from S101F/L/M/W/Y, S103L, T106I/L, G131I or G133K. According to a particular embodiment, the protease variant comprises at least three substitutions at positions S101+S103+G133, preferably S101F+S103L+G133K. According to another particular embodiment, the protease variant comprises at least three substitutions at positions S101+T106+G133, preferably S101F+T106I+G133K. In a preferred embodiment, the protease variant comprises at least three substitutions at positions S101+S103+T106, preferably S101F+S103L+T106I/L.

According to a particular embodiment, the protease comprises at least the combination of substitutions selected from S101F+S103L+G133K, S101F+S103L+T106I, S101F+T106I+G133K, S101F+S103L+T106L, preferably S101F+S103L+T106I or S101F+S103L+T106L.

In a particular embodiment, the protease has the amino acid sequence as set forth in SEQ ID No 1, except the combination of substitutions S101F+S103L+G133K (V10), S101F+S103L+T106I (V8), S101F+T106I+G133K (V11) or S101F+S103L+T106L (V19).

According to a particular embodiment, the protease comprises at least the combination of substitutions selected from S101F+S103L+T106I+G133K or S101F+S103L+T106I+G131I.

In a particular embodiment, the protease has the amino acid sequence as set forth in SEQ ID No 1, except the combination of substitutions S101F+S103L+T106I+G133K (V12) or S101F+S103L+T106I+G131I (V13).

In a particular embodiment, the protease variant of the invention further comprises at least one amino acid substitution at a position selected from D12, L21, T175, S194, H197, G212, I217 or R247 wherein the positions are numbered by reference to the amino acid sequence set forth in SEQ ID No 1, preferably at least one substitution selected from D12C+L21C, T175C+R247C, S194P, H197D, G212N, or I217K.

In a particular embodiment, the protease has the amino acid sequence as set forth in SEQ ID No 28 and at least one substitution at a position selected from S101, S103, T106, G131 or G133 wherein the positions are numbered by reference to the amino acid sequence set forth in SEQ ID No 1. Preferably, the protease has the amino acid sequence as set forth in SEQ ID No 28 and at least one amino acid substitution at a position selected from S101F/L/M/W/Y, S103L, T106I/L, G131I, or G133K, wherein the positions are numbered by reference to the amino acid sequence set forth in SEQ ID No 1, more preferably at least a substitution selected from S101F/L/M/W/Y, more preferably at least the substitution S101F.

Propeptide

Advantageously, the protease variant and/or the parent protease comprises at the N-terminal end an amino acid sequence acting as a "propeptide" (SEQ ID No 2) which is at least partially responsible for the 3D folding and the maturation of the protease.

Particularly, the protease variant and/or the parent protease comprises at the N-terminal end an amino acid sequence, which has at least 75%, 80%, 85%, 90%, 95%, 96%, 97%, 98%, 99% or 100% identity to the full length amino acid sequence set forth in SEQ ID No 2.

According to a particular embodiment, the protease variant and/or the parent protease comprises at the N-terminal end an amino acid sequence which has at least 75%, 80%, 85%, 90%, 95%, 96%, 97%, 98% or 99% identity to the full length amino acid sequence set forth in SEQ ID No 2, and has at least one amino acid substitution at a position selected from M8, D75, A76, I78 or D81 wherein the positions are numbered by reference to the amino acid sequence set forth in SEQ ID No 2. According to the invention, the targeted amino acid(s) may be replaced by any one of the other amino acids selected from standard naturally-occurring amino acid residues, rare naturally occurring amino acid residues and non-naturally occurring amino acid residue. Preferably, the targeted amino acid(s) may be replaced by any one of the 19 other amino acids.

Polyester Degrading Activity

It is an object of the invention to provide new enzymes having a protease activity.

In a particular embodiment, the protease of the invention has a polyester degrading activity, preferably a polylactic acid degrading activity. Preferably, the protease of the invention exhibits an increased polyester degrading activity compared to the protease of SEQ ID No 1.

Advantageously, the protease variant and/or the parent protease of the invention exhibits a polyester degrading activity at least in a range of temperatures from 10° C. to 90° C., preferably from 20° C. to 70° C., more preferably from 30° C. to 60° C., even more preferably at 45° C. In a particular embodiment, the polyester degrading activity is still measurable at a temperature between 40° C. and 60° C., preferably between 50° C. and 60° C. In another particular embodiment, the polyester degrading activity is still measurable at a temperature between 10° C. and 30° C., preferably between 15° C. and 28° C., corresponding to the mean temperature in the natural environment.

In a particular embodiment, the protease variant of the invention has an increased polyester degrading activity at a given temperature, compared to the protease of SEQ ID No 1, and more particularly at a temperature between 20° C. and 80° C., more preferably between 30° C. and 70° C., even more preferably between 40° C. and 60° C., even more preferably at 45° C. In a particular embodiment, the protease variant has a polyester degrading activity at 45° C. at least 5% higher than the polyester degrading activity of the protease of SEQ ID No 1, preferably at least 10%, 20%, 50%, 100%, 200%, 300%, 500% or higher.

In a particular embodiment, the protease variant of the invention has an increased polyester degrading activity, compared to the protease of SEQ ID No 1, at a temperature between 10° C. and 30° C., more preferably between 15° C. and 30° C., even more preferably between 20° C. and 30° C., even more preferably at 28° C. In a particular embodiment, the protease variant has a polyester degrading activity at 28° C. at least 5% higher than the polyester degrading activity of the protease of SEQ ID No 1, preferably at least 10%, 20%, 50%, 100%, 200%, 300%, 500% or higher.

In a particular embodiment, the protease variant of the invention exhibits a measurable polyester degrading activity at least in a range of pH from 5 to 11, preferably in a range of pH from 7 to 10, more preferably in a range of pH from 7.5 to 9, even more preferably at both pH 7.5 and 9.

Thermostability

Advantageously, the thermostability of the variant proteases of the invention is not impaired compared to the thermostability of the parent protease of SEQ ID No 1. More advantageously, the thermostability of the variants is improved compared to the thermostability of the parent protease. Within the context of the invention, the term "improved thermostability" indicates an increased ability of the enzyme to resist to changes in its chemical and/or physical structure at high temperatures, and more particularly at temperature between 40° C. and 90° C., such as 70° C., as compared to the protease of SEQ ID No 1. In particular, the proteases of the present invention can have an increased residual degrading activity at a temperature between 40° C. and 90° C., such as 70° C., as compared to the protease of SEQ ID No 1. In particular, the proteases of the present invention can have an increased half-life at a temperature between 40° C. and 90° C., such as 70° C., as compared to the protease of SEQ ID No 1. Particularly, the variant of the invention shows an improved thermostability during an extrusion process, and more particularly during an extrusion process implemented at a temperature comprised between 50° C. and 250° C., preferably between 130° C. and 180° C.

The thermostability of a protein may be evaluated by the one skilled in the art, according to methods known per se in the art. For instance, thermostability can be assessed by measuring the residual protease activity and/or the residual polyester depolymerization activity (i.e., polyester degrading activity) of the enzyme after incubation at different temperatures. The ability to perform multiple rounds of polyester's depolymerization assays at different temperatures can also be evaluated. A rapid and qualitative test may consist of the evaluation, by halo diameter measurement, of the enzyme ability to degrade a solid polyester compound dispersed in an agar plate after incubation at different temperatures. Alternatively or in addition, a Differential Scanning Fluorimetry (DSF) may be performed to assess the thermostability of a protein/enzyme. In the context of the invention, circular dichroism is used to quantify the change in thermal denaturation temperature of a protein and thereby to determine its melting temperature (Tm). In the context of the invention the "melting temperature (Tm)" of a given protein corresponds to the temperature at which half of said protein is denatured (unfolded or misfolded). The Tm may be measured using circular dichroism as exposed in the experimental part.

Advantageously, the protease of the invention exhibits a higher or equivalent melting temperature (Tm) as compared to the protease of SEQ ID No 1. In a particular embodiment, the protease of the invention exhibits a melting temperature (Tm) above 40° C., preferably above 45° C., more preferably above 50° C.

Nucleic Acids, Expression Cassette, Vector, Host Cell

It is a further object of the invention to provide a nucleic acid encoding a protease as defined above.

As used herein, the term "nucleic acid", "nucleic sequence," "polynucleotide", "oligonucleotide" and "nucleotide sequence" are used interchangeably and refer to a sequence of deoxyribonucleotides and/or ribonucleotides. The nucleic acids can be DNA (cDNA or gDNA), RNA, or a mixture thereof. It can be in single stranded form or in duplex form or a mixture thereof. It can be of recombinant, artificial and/or synthetic origin and it can comprise modified nucleotides, comprising for example a modified bond, a modified purine or pyrimidine base, or a modified sugar. The nucleic acids of the invention can be in isolated or purified form, and made, isolated and/or manipulated by techniques known per se in the art, e.g., cloning and expression of cDNA libraries, amplification, enzymatic synthesis or recombinant technology. The nucleic acids can also be synthesized in vitro by well-known chemical synthesis techniques, as described in, e.g., Belousov (1997) Nucleic Acids Res. 25:3440-3444.

The invention also encompasses nucleic acids which hybridize, under stringent conditions, to a nucleic acid encoding a protease as defined above. Preferably, such stringent conditions include incubations of hybridization filters at about 42° C. for about 2.5 hours in 2×SSC/0.1% SDS, followed by washing of the filters four times of 15 minutes in 1×SSC/0.1% SDS at 65° C. Protocols used are described in such reference as Sambrook et al. (Molecular Cloning: a Laboratory Manual, Cold Spring Harbor Press, Cold Spring Harbor N.Y. (1988)) and Ausubel (Current Protocols in Molecular Biology (1989)).

The invention also encompasses nucleic acids encoding a protease of the invention, wherein the sequence of said nucleic acids, or a portion of said sequence at least, has been engineered using optimized codon usage.

Alternatively, the nucleic acids according to the invention may be deduced from the sequence of the protease according to the invention and codon usage may be adapted according to the host cell in which the nucleic acids shall be transcribed. These steps may be carried out according to methods well known to one skilled in the art and some of which are described in the reference manual Sambrook et al. (Sambrook et al., 2001).

Nucleic acids of the invention may further comprise additional nucleotide sequences, such as regulatory regions, i.e., promoters, enhancers, silencers, terminators, signal peptides and the like that can be used to cause or regulate expression of the polypeptide in a selected host cell or system. Alternatively, or in addition, nucleic acids of the invention may further comprise additional nucleotide sequences encoding fusion proteins, such as maltose binding protein (MBP) or glutathion S transferase (GST) that can be used to favor polypeptide expression and/or solubility.

The present invention further relates to an expression cassette comprising a nucleic acid according to the invention operably linked to one or more control sequences that direct the expression of said nucleic acid in a suitable host cell. The term "expression cassette" denotes a nucleic acid construct comprising a coding region, i.e. a nucleic acid of the invention, and a regulatory region, i.e. comprising one or more control sequences (e.g., transcriptional promoter and/or transcription terminator). The control sequence may include a promoter that is recognized by a host cell or an in vitro expression system for expression of a nucleic acid encoding a protease of the present invention. The promoter contains transcriptional control sequences that mediate the expression of the enzyme. The promoter may be any polynucleotide that shows transcriptional activity in the host cell including mutant, truncated, and hybrid promoters, and may be obtained from genes encoding extracellular or intracellular polypeptides either homologous or heterologous to the host cell. The control sequence may also be a transcription terminator, which is recognized by a host cell to terminate transcription. The terminator is operably linked to the 3'-terminus of the nucleic acid encoding the protease. Any terminator that is functional in the host cell may be used in the present invention. Typically, the expression cassette comprises, or consists of, a nucleic acid according to the invention operably linked to a transcriptional promoter and a transcription terminator.

The invention also relates to a vector comprising a nucleic acid or an expression cassette as defined above.

The term "vector" refers to DNA or RNA molecule used as a vehicle to transfer recombinant genetic material into a host cell. The vector may be linear or circular, single- or double-stranded DNA or RNA. The vector may be integrative or extrachromosomal, or autoreplicative. Preferably, the expression vector is a linear or circular double stranded DNA molecule. The major types of vectors are plasmids, bacteriophages, viruses, fosmids, cosmids, and artificial chromosomes. The vector itself is generally a DNA or RNA sequence that consists of an insert (a heterologous nucleic acid sequence, transgene) and a larger sequence that serves as the "backbone" of the vector. The purpose of a vector which transfers genetic information to the host is typically to isolate, multiply, or express the insert in the target cell. Vectors called expression vectors (expression constructs) are specifically adapted for the expression of the heterologous sequences in the target cell, and generally have a promoter sequence that drives expression of the heterologous sequences encoding a polypeptide. As used herein, the term "expression vector" means a DNA or RNA molecule that comprises an expression cassette of the invention. Generally, the regulatory elements that are present in an expression vector include a transcriptional promoter, a ribosome binding site, a terminator, and optionally present operator. Preferably, an expression vector also contains an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses. Expression vectors providing suitable levels of polypeptide expression in different hosts are well known in the art. The choice of the vector will typically depend on the compatibility of the vector with the host cell into which the vector is to be introduced. Preferably, the expression vector is a linear or circular double stranded DNA molecule.

It is another object of the invention to provide a host cell comprising a nucleic acid, an expression cassette or a vector as described above. The present invention thus relates to the use of a nucleic acid, expression cassette or vector according to the invention to transform, transfect or transduce a host cell. The choice of the vector will typically depend on the compatibility of the vector with the host cell into which it must be introduced.

According to the invention, the host cell may be transformed, transfected or transduced in a transient or stable manner. The expression cassette or vector of the invention is introduced into a host cell so that the cassette or vector is maintained as a chromosomal integrant or as a self-replicating extra-chromosomal vector. The term "host cell" also encompasses any progeny of a parent host cell that is not identical to the parent host cell due to mutations that occur during replication. The host cell may be any cell useful in the production of a variant of the present invention, e.g., a prokaryote or a eukaryote. The prokaryotic host cell may be any Gram-positive or Gram-negative bacterium. The host cell may also be a eukaryotic cell, such as a yeast, fungal, mammalian, insect or plant cell. In a particular embodiment, the host cell is selected from the group of *Escherichia coli*, *Bacillus*, *Streptomyces*, *Trichoderma*, *Aspergillus*, *Saccharomyces*, *Pichia*, *Thermus*, *Actinomadura* or *Yarrowia*.

The nucleic acid, expression cassette or expression vector according to the invention may be introduced into the host cell by any method known by the skilled person, such as electroporation, conjugation, transduction, competent cell transformation, protoplast transformation, protoplast fusion, biolistic "gene gun" transformation, PEG-mediated transformation, lipid-assisted transformation or transfection, chemically mediated transfection, lithium acetate-mediated transformation, liposome-mediated transformation.

Optionally, more than one copy of a nucleic acid, cassette or vector of the present invention may be inserted into a host cell to increase production of the variant.

In a particular embodiment, the host cell is a recombinant microorganism. The invention indeed allows the engineering of microorganisms with improved capacity to degrade polyester containing material. For instance, the sequence of the invention may be used to complement a wild type strain of a fungus or bacterium already known as able to degrade polyester, in order to improve and/or increase the strain capacity.

Production of Protease Variants

It is another object of the invention to provide a method of producing a protease variant of the invention, comprising expressing a nucleic acid encoding the protease and optionally recovering the protease.

In particular, the present invention relates to in vitro methods of producing a protease of the present invention comprising (a) contacting a nucleic acid, cassette or vector of the invention with an in vitro expression system; and (b) recovering the protease produced. In vitro expression systems are well-known by the person skilled in the art and are commercially available.

Preferably, the method of production comprises (a) culturing a host cell that comprises a nucleic acid encoding a protease of the invention under conditions suitable to express the nucleic acid; and optionally (b) recovering said protease from the cell culture.

Advantageously, the host cell is a recombinant *Bacillus*, recombinant *E. coli*, recombinant *Aspergillus*, recombinant *Trichoderma*, recombinant *Streptomyces*, recombinant *Saccharomyces*, recombinant *Pichia*, recombinant *Thermus*, recombinant *Actinomadura* or recombinant *Yarrowia*. Preferably, the host cell is a recombinant *Bacillus*.

The host cells are cultivated in a nutrient medium suitable for production of polypeptides, using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the enzyme to be expressed and/or isolated. The cultivation takes place in a suitable nutrient medium, from commercial suppliers or prepared according to published compositions (e.g., in catalogues of the American Type Culture Collection) or any other culture medium suitable for cell growth.

If the protease is excreted into the nutrient medium, the protease can be recovered directly from the culture supernatant. Conversely, the protease can be recovered from cell lysates or after permeabilisation. The protease may be recovered using any method known in the art. For example, the protease may be recovered from the nutrient medium by conventional procedures including, but not limited to, collection, centrifugation, filtration, extraction, spray-drying, evaporation, or precipitation. Optionally, the protease may be partially or totally purified by a variety of procedures known in the art including, but not limited to, thermal chock, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction to obtain substantially pure polypeptides.

The protease may be used as such, in purified form, either alone or in combination with additional enzymes, to catalyze enzymatic reactions involved in the degradation and/or recycling of polyester(s) and/or polyester containing materials, such as plastic products containing polyester. The protease may be in soluble form, or on solid phase. In particular, it may be bound to cell membranes or lipid vesicles, or to synthetic supports such as glass, plastic, polymers, filter, membranes, e.g., in the form of beads, columns, plates and the like.

Composition

It is a further object of the invention to provide a composition comprising a protease or a host cell of the invention or extract thereof. In the context of the invention, the term "composition" encompasses any kind of compositions comprising a protease or host cell of the invention. In a particular embodiment, the protease is in isolated or at least partially purified form.

The composition may be liquid or dry, for instance in the form of a powder. In some embodiments, the composition is a lyophilisate. For instance, the composition may comprise the protease and/or host cells encoding the protease of the invention or extract thereof containing said protease, and optionally excipients and/or reagents etc. Appropriate excipients encompass buffers commonly used in biochemistry, agents for adjusting pH, preservatives such as sodium benzoate, sodium sorbate or sodium ascorbate, conservatives, protective or stabilizing agents such as starch, dextrin, arabic gum, salts, sugars e.g. sorbitol, trehalose or lactose, glycerol, polyethyleneglycol, polyethene glycol, polypropylene glycol, propylene glycol, divalent ions such as calcium, sequestering agent such as EDTA, reducing agents, amino acids, a carrier such as a solvent or an aqueous solution, and the like. The composition of the invention may be obtained by mixing the protease with one or several excipients.

The composition of the invention may comprise from 0.1% to 99.9%, preferably from 0.1% to 50%, more preferably from 0.1% to 30%, even more preferably from 0.1% to 5% by weight of the protease of the invention and from 0.1% to 99.9%, preferably from 50% to 99.9%, more preferably from 70% to 99.9%, even more preferably from 95% to 99.9% by weight of excipient(s). A preferred composition comprises between 0.1 and 5% by weight of the protease of the invention. In another embodiment, the composition of the invention may comprise from 0.1% to 40%, more preferably from 1% to 30%, even more preferably from 5% to 25% by weight of the protease of the invention and from 60% to 99.9%, preferably from 70% to 99%, more preferably from 75% to 95% by weight of excipient(s).

In a particular embodiment, the composition may further comprise additional polypeptide(s) exhibiting an enzymatic activity. The amounts of protease of the invention will be easily adapted by those skilled in the art depending e.g., on the nature of the polyester and/or polyester containing material to degrade and/or the additional enzymes/polypeptides contained in the composition.

In a particular embodiment, the protease of the invention is solubilized in an aqueous medium together with one or several excipients, especially excipients which are able to stabilize or protect the polypeptide from degradation. For instance, the protease of the invention may be solubilized in water, eventually with additional components, such as glycerol, sorbitol, dextrin, starch, glycol such as propanediol, salt, etc. The resulting mixture may then be dried so as to obtain a powder. Methods for drying such mixture are well known to the one skilled in the art and include, without limitation, lyophilisation, freeze-drying, spray-drying, supercritical drying, down-draught evaporation, thin-layer evaporation, centrifugal evaporation, conveyer drying, fluidized bed drying, drum drying or any combination thereof.

In a further particular embodiment, the composition of the invention comprises at least one host cell expressing a protease of the invention, or an extract thereof. An "extract of a cell" designates any fraction obtained from a cell, such as cell supernatant, cell debris, cell walls, DNA extract, enzymes or enzyme preparation or any preparation derived from cells by chemical, physical and/or enzymatic treatment, which is essentially free of living cells. Preferred extracts are enzymatically-active extracts. The composition of the invention may comprise one or several host cells of the invention or extract thereof containing the protease of the invention, and optionally one or several additional cells.

In a particular embodiment, the composition consists or comprises a lyophilized culture medium of a recombinant microorganism expressing and/or excreting a protease of the invention. In a particular embodiment, the powder comprises the protease of the invention and a stabilizing/solubilizing amount of glycerol, sorbitol or dextrin, such as maltodextrine and/or cyclodextrine, starch, Arabic gum, glycol such as propanediol, and/or salt.

Uses of the Proteases

It is a further object of the invention to provide methods using a protease of the invention for degrading and/or recycling in aerobic or anaerobic conditions polyester and/or polyester containing material, as plastic products made of or containing polyesters and/or producing biodegradable plastic products containing polyester. The proteases of the invention are particularly useful for producing biodegradable plastic products containing PLA and/or for degrading PLA and a plastic product comprising PLA.

It is therefore an object of the invention to use a protease of the invention, or corresponding host cell or extract thereof containing such protease, or composition, for the enzymatic degradation of a polyester or a polyester containing material, such as PLA or a PLA containing material.

It is another object of the invention to provide a method for degrading a polyester or a plastic product containing at least one polyester, wherein the polyester or the plastic product is contacted with a protease or host cell or composition of the invention. Advantageously, polyester(s) and/or polyester(s) of the polyester containing material is (are) depolymerized up to monomers and/or oligomers. In an embodiment of the method of degradation, at least one polyester is degraded to yield repolymerizable monomers and/or oligomers, which are advantageously retrieved in order to be used. In a preferred embodiment of the method of degradation, at least PLA is degraded to yield repolymerizable monomers and/or oligomers of lactic acid (LA), which are advantageously retrieved in order to be used for instance to produce new polymers of PLA.

In an embodiment, polyester(s) and/or polyester(s) of the polyester containing material is (are) fully degraded.

In a particular embodiment, the polyester is selected from polylactic acid (PLA), poly(glycolic acid) (PGA), poly (lactic-co-glycolic acid) (PLGA), polytrimethylene terephthalate (PTT), polybutylene terephthalate (PBT), polyethylene isosorbide terephthalate (PEIT), polyethylene terephthalate (PET), polyhydroxyalkanoate (PHA), polybutylene succinate (PBS), polybutylene succinate adipate (PBSA), polybutylene adipate terephthalate (PBAT), polyethylene furanoate (PEF), polycaprolactone (PCL), poly (ethylene adipate) (PEA) and blends/mixtures thereof, preferably polylactic acid.

In a particular embodiment, the plastic product comprises at least one polyester selected from polylactic acid (PLA), polytrimethylene terephthalate (PTT), polybutylene terephthalate (PBT), polyethylene isosorbide terephthalate (PEIT), polyethylene terephthalate (PET), polyhydroxyalkanoate (PHA), polybutylene succinate (PBS), polybutylene succinate adipate (PBSA), polybutylene adipate terephthalate (PBAT), polyethylene furanoate (PEF), polycaprolactone (PCL), poly(ethylene adipate) (PEA) and blends/mixtures of these materials, preferably polylactic acid.

In a particular embodiment, PLA or a plastic product containing PLA is contacting with a protease or host cell of the invention and PLA is degraded to monomers and/or oligomers of lactic acid. In a preferred embodiment, monomers and/or oligomers of lactic acid are recovered for recycling, polymerizing PLA or methanisation for instance.

The invention also relates to a method of producing monomers and/or oligomers from a polyester or polyester containing material, comprising exposing a polyester or polyester containing material to a protease of the invention, or corresponding host cell or extract thereof, or composition, and optionally recovering monomers and/or oligomers. The method of the invention is particularly useful for producing monomers such as lactic acid from plastic product containing PLA.

The time required for degrading a polyester or polyester containing material may vary depending on the polyester or polyester containing material itself (i.e., nature and origin of the plastic product, its composition, shape etc.), the type and amount of protease used, as well as various process parameters (i.e., temperature, pH, additional agents, etc.). One skilled in the art may easily adapt the process parameters to the polyester containing material.

Advantageously, the degrading process is implemented at a temperature comprised between 10° C. and 90° C., preferably between 20° C. to 70° C., more between 30° C. to 60° C., even more preferably at 45° C. More generally, the temperature is maintained below an inactivating temperature, which corresponds to the temperature at which the protease is inactivated and/or the recombinant microorganism does no more synthesize the protease. Preferably, the temperature is maintained below the glass transition temperature (Tg) of the polyester in the polyester containing material. In this embodiment, the degrading process is implemented at a temperature comprised below 80° C., preferably below 70° C., more preferably below 60° C., more preferably below 50° C., even more preferably at 45° C. More particularly, the process is implemented in a continuous way, at a temperature at which the protease can be used several times and/or recycled.

Advantageously, the degrading process is implemented at a pH comprised between 5 and 11, preferably at a pH between 7 and 10, more preferably at a pH between 7.5 and 9, even more preferably at pH 7.5 or pH 9.

In a particular embodiment, the polyester or polyester containing material may be pretreated prior to be contacted with the protease, in order to physically change its structure, so as to increase the surface of contact between the polyester and the enzyme.

Optionally, monomers and/or oligomers resulting from the depolymerization may be recovered, sequentially or continuously. A single type of monomers and/or oligomers or several different types of monomers and/or oligomers may be recovered, depending on the starting polyester containing material.

The recovered monomers and/or oligomers may be further purified, using all suitable purifying methods and conditioned in a repolymerizable form. Examples of purifying methods include stripping process, separation by aqueous solution, steam selective condensation, filtration and concentration of the medium after the bioprocess, separation, distillation, vacuum evaporation, extraction, electrodialysis, adsorption, ion exchange, precipitation, crystallization, concentration and acid addition dehydration and precipitation, nanofiltration, acid catalyst treatment, semi continuous mode distillation or continuous mode distillation, solvent extraction, evaporative concentration, evaporative crystallization, liquid/liquid extraction, hydrogenation, azeotropic distillation process, adsorption, column chromatography, simple vacuum distillation and microfiltration, combined or not.

The repolymerizable monomers and/or oligomers may then be used for instance to synthesize polyesters. Advantageously, polyesters of same nature are repolymerized. However, it is possible to mix the recovered monomers and/or oligomers with other monomers and/or oligomers, in order for instance to synthesize new copolymers. Alternatively, the recovered monomers may be used as chemical intermediates in order to produce new chemical compounds of interest.

It is a further object of the invention to provide a polyester or polyester containing material in which a protease of the invention and/or a recombinant microorganism expressing and/or excreting said protease and/or extract thereof containing such protease, and/or a composition of the invention is/are included. In a particular embodiment, such polyester containing material may be a plastic compound, a masterbatch composition and/or a plastic product. In the context of the invention, a "masterbatch composition" refers to a concentrated mixture of selected ingredients (e.g., active agents, additives, etc.) that can be used for introducing said ingredients into plastic compound or product in order to impart desired properties thereto. Masterbatch compositions may be solid or liquid. Preferably, masterbatch compositions of the invention contain at least 10% by weight of active ingredients, more preferably of protease or composition of the invention.

It is thus a further object of the invention to provide a plastic compound containing a protease of the invention and/or a recombinant microorganism expressing and/or excreting said protease or extract thereof containing such protease and/or a composition of the invention and at least one polyester. In a particular embodiment, the polyester is polylactic acid (PLA), preferably poly(L-lactic acid) (PLLA), poly(D-lactic acid) (PDLA) or poly(DL-lactic acid) (PDLLA). In a particular embodiment, the plastic compound may contain an additional polymer, preferably selected from polyesters such as PBAT, PCL, PET; polyolefins such as polyethylene, polypropylene or natural polymers such as starch, cellulose or flour; and blends/mixtures thereof. More particularly, the plastic compound may contain additional polymers selected from PBAT, flour or starch. In another particular embodiment, the polyester is polycaprolactone (PCL).

It is thus a further object of the invention to provide a masterbatch composition containing a protease of the invention and/or a recombinant microorganism expressing and/or excreting said protease or extract thereof containing such protease and/or a composition of the invention, and at least one polyester. In a particular embodiment, the polyester is polylactic acid (PLA), preferably poly(L-lactic acid) (PLLA), poly(D-lactic acid) (PDLA) or poly(DL-lactic acid) (PDLLA). In another particular embodiment, the polyester is preferably polycaprolactone (PCL).

In particular, the invention relates to a process for producing such polyester containing material (i.e., plastic compound, masterbatch composition or plastic product) comprising a step of mixing a polyester and a protease and/or recombinant microorganism of the invention or extract thereof containing such protease and/or a composition of the invention, able to degrade said polyester, at a temperature at which the polyester is in a partially or totally molten state so that the protease/microorganisms are integrated into the very structure of the polyester containing material. In a particular embodiment, the process is an extrusion process.

For instance, the protease and/or the composition of the invention and the polyester may be mixed at a temperature between the glass transition temperature and the melting point of the polyester. Alternatively, the protease/composition of the invention and the polyester may be mixed at a temperature corresponding to the melting point of said polyester, or above. In a particular embodiment, the protease/composition and the polyester are mixed at a temperature between 40° C. and 250° C., preferably between 50° C. and 180° C. Alternatively, the polypeptide/composition and the polyester are mixed at a temperature above 40° C., preferably above 50° C., even more preferably above 60° C.

In a preferred embodiment, the polyester is selected from polylactic acid (PLA), and the protease/composition and PLA are mixed at a temperature between 60° C. and 250° C., preferably between 100° C. and 200° C., more preferably between 130° C. and 180° C., even more preferably between 140° C. and 160° C. Alternatively, the protease/composition and PLA are mixed at a temperature above 80° C., preferably, above 100° C., even more preferably above 130° C., and below 180° C.

In another preferred embodiment, the polyester is selected from polycaprolactone (PCL), and the protease/composition and PCL are mixed at a temperature between 40° C. and 100° C., preferably between 50° C. and 80° C. Alternatively, the protease/composition and PCL are mixed at a temperature above 40° C., preferably, above 50° C., even more preferably above 55° C., and below 80° C.

More preferably, the mixing step is performed using extrusion, twin screw extrusion, single screw extrusion, injection-molding, casting, thermoforming, rotary molding, compression, calendering, ironing, coating, stratification, expansion, pultrusion, extrusion blow-molding, extrusion-swelling, compression-granulation, water-in-oil-in-water double emulsion evaporation, 3D printing or any techniques known by person skilled in the art.

The resulting plastic compound, masterbatch composition or plastic product integrates protease/microorganism or composition of the invention embedded in the mass of the compound, masterbatch composition or plastic product.

Advantageously, such plastic compound, masterbatch composition can be used for the production of polyester containing materials and/or plastic article that will thus include the polypeptide of the invention.

In a particular embodiment, the resulting plastic compound, masterbatch composition or plastic article is a biodegradable plastic compound, masterbatch composition or plastic article complying with at least one of the relevant standards and/or labels known by the person skilled in the art, such as standard EN 13432, standard ASTM D6400, OK Biodegradation Soil (Label Vinçotte), OK Biodegradation Water (Label Vinçotte), OK Compost (Label Vinçotte), OK Home Compost (Label Vinçotte).

Advantageously, the degrading process of the polyester containing material (i.e., plastic compound, masterbatch composition or plastic product) is implemented at a temperature comprised between 10° C. and 50° C., preferably between 15° C. and 40° C., more preferably between 20° C. and 30° C., more preferably at 28° C., +/−2° C.

Alternatively, the degrading process of the polyester containing material (i.e., plastic compound, masterbatch composition or plastic product) is implemented at a temperature comprised between 50° C. and 60° C., more preferably at 55° C., +/−2° C.

Interestingly, a protease comprising an amino acid sequence having at least 75%, 80%, 85%, 90%, 95%, 96%, 97%, 98%, 99% or 100% identity to the full length amino acid sequence set forth in SEQ ID No 1, may be used in the applications cited above.

Classically, a protease of the invention or a protease comprising an amino acid sequence having at least 75%, 80%, 85%, 90%, 95%, 96%, 97%, 98%, 99% or 100% identity to the full length amino acid sequence set forth in SEQ ID No 1, may be used in detergent, food, animal feed and pharmaceutical applications.

More particularly, a protease of the invention or a protease comprising an amino acid sequence having at least 75%, 80%, 85%, 90%, 95%, 96%, 97%, 98%, 99% or 100% identity to the full length amino acid sequence set forth in SEQ ID No 1, may be used as a component of a detergent composition.

Detergent compositions include, without limitation, hand or machine laundry detergent compositions, such as laundry additive composition suitable for pre-treatment of stained fabrics and rinse added fabric softener composition, detergent composition for use in general household hard surface cleaning operations, detergent compositions for hand or machine dishwashing operations.

In a particular embodiment, a protease of the invention or protease comprising an amino acid sequence having at least 75%, 80%, 85%, 90%, 95%, 96%, 97%, 98%, 99% or 100% identity to the full length amino acid sequence set forth in SEQ ID No 1, may be used as a detergent additive. The invention thus provides detergent compositions comprising a protease of the invention or protease comprising an amino acid sequence having at least 75%, 80%, 85%, 90%, 95%, 96%, 97%, 98%, 99% or 100% identity to the full length amino acid sequence set forth in SEQ ID No 1.

The present invention is also directed to methods for using a protease of the invention or protease comprising an amino acid sequence having at least 75%, 80%, 85%, 90%, 95%, 96%, 97%, 98%, 99% or 100% identity to the full length amino acid sequence set forth in SEQ ID No 1, in animal feed, as well as to feed compositions and feed additives comprising a protease of the invention or protease comprising an amino acid sequence having at least 75%, 80%, 85%, 90%, 95%, 99% or 100% identity to the full length amino acid sequence set forth in SEQ ID No 1. The terms "feed" and "feed composition" refer to any compound, preparation, mixture, or composition suitable for, or intended for intake by an animal. In another particular embodiment, the protease of the invention or protease comprising an amino acid sequence having at least 75%, 80%, 85%, 90%, 95%, 96%, 97%, 98%, 99% or 100% identity to the full length amino acid sequence set forth in SEQ ID No 1 is used to hydrolyze proteins, and to produce hydrolysates comprising peptides. Such hydrolysates may be used as feed composition or feed additives.

The invention also relates to a method of surface hydrolysis or surface functionalization of a polyester containing material, comprising exposing a polyester containing material to a protease of the invention, or protease comprising an amino acid sequence having at least 75%, 80%, 85%, 90%, 95%, 96%, 97%, 98%, 99% or 100% identity to the full length amino acid sequence set forth in SEQ ID No 1, or corresponding recombinant cell or extract thereof, or composition. The method of the invention is particularly useful for increasing hydrophilicity, or water absorbency, of a polyester material. Such increased hydrophilicity may have particular interest in textiles production, electronics and biomedical applications.

EXAMPLES

Example 1—Construction, Expression and Purification of Proteases 1.1 Construction The gene (nucleic SEQ ID No 5) encoding for the non-matured parent protease (SEQ ID No 4 corresponding to SEQ ID No 2+SEQ ID No 1) was cloned in the plasmid pET26b+ (EMD Millipore, Billerica, Mass., USA), in frame with sequences encoding PelB signal peptide (SEQ ID No 3 MKYLLPTAAAGLLLLAAQPAMA) upstream of the gene and a 6× histidine tag (SEQ ID No 6 LEHHHHHH) downstream of the gene. *E. coli* One Shot® BL21 DE3 (Life technologies, Carlsbad, Calif., USA) was transformed with the constructed plasmid. The obtained strain expresses the wild-type protease with a PelB leader sequence at the N-terminal and a 6× histidine Tag at the C-terminal of the protein. QuikChange II Site-Directed Mutagenesis kit was used according to the recommendations of the supplier to construct the variants (Santa Clara, Calif., USA). Table 1 gives forward and reverse primers used for the site-directed mutagenesis.

TABLE 1

Forward and reverse primers used for site-directed mutagenesis of the gene coding for parent protease for the production of protease variants of the invention

| | Sequences |
|---|---|
| PAM S101F forward (SEQ ID No 7) | 5'-GTCCGAGTGCTCAACTGTTTCGGCTCTGGTACCACT-3' |
| PAM S101L forward (SEQ ID No 8) | 5'-GTC CGA GTG CTC AAC TGT CTG GGCTCTGGTACCACT-3' |
| PAM S101M forward (SEQ ID No 9) | 5'-GTC CGA GTG CTC AAC TGT ATG GGCTCTGGTACCACT-3' |
| PAM S101W forward (SEQ ID No 10) | 5'-GTC CGA GTG CTC AAC TGT TGG GGCTCTGGTACCACT-3' |
| PAM S101Y forward (SEQ ID No 11) | 5'-GTC CGA GTG CTC AAC TGT TAC GGCTCTGGTACCACT-3' |
| PAM S101 reverse (SEQ ID No 12) | 5'-ACAGTTGAGCACTCGGACACCTCGCAGGTTCACAGC-3' |
| PAM S103L forward (SEQ ID No 13) | 5'-TG CTC AAC TGT TCC GGC CTG GGTACCACTTCCGGA-3' |
| PAM S103 reverse (SEQ ID No 14) | 5'-GCCGGAACAGTTGAGCACTCGGACACCTCGCAG-3' |
| PAM T106I forward (SEQ ID No 15) | 5'-GTTCCGGCTCTGGTACCATCTCCGGAGTCATCGCT-3' |
| PAM T106L forward (SEQ ID No 16) | 5'-GTTCCGGCTCTGGTACC CTG TCCGGAGTCATCGCT-3' |
| PAM T106 reverse (SEQ ID No 17) | 5'-GGTACCAGAGCCGGAACAGTTGAGCACTCGGACACC-3' |
| PAM G131I forward (SEQ ID No 18) | 5'-CGCTAACATGTCCCTGATCGGTGGATACTCCTCT-3' |
| PAM G131 reverse (SEQ ID No 19) | 5'-CAGGGACATGTTAGCGACGGCGGGCTTAACATG-3' |
| PAM G133K forward (SEQ ID No 20) | 5'-CTAACATGTCCCTGGGCGGTAAGTACTCCTCTTCGC-3' |
| PAM G133 reverse (SEQ ID No 21) | 5'-GCCCAGGGACATGTTAGCGACGGCGGGCTTAAC-3' |
| PAM_S101F_S103L forward (SEQ ID No 22) | 5'-GAGTGCTCAACTGTTTCGGCCTGGGTA-3' |
| PAM_S101F_S103L reverse (SEQ ID No 23) | 5'-TCGGAAGTGGTACCCAGGCCGAAACAG-3' |
| PAM_S101F_S103L_T106I forward (SEQ ID No 24) | 5'-ACTGTTTCGGCCTGGGTACCATCTCCGGAG-3' |
| PAM_S101F_S103L_T106I reverse (SEQ ID No 25) | 5'-GGAGATGGTACCCAGGCCGAAACAGTTGAGC-3' |
| PAM_T106L bis forward (SEQ ID No 26) | 5'-GGTACCCTGTCCGGAGTCATCG-3' |
| PAM_S103L_T106L reverse (SEQ ID No 27) | 5'-TCCGGACAGGGTACCCAGGC-3' |

Mutated codons are underlined 1.2 Expression and Purification of the Proteases

Recombinant expression of the strains expressing the wild-type protease and variants thereof was realized in 100 mL TB medium at 37° C. during 4 hours then at 21° C. after IPTG addition at final concentration of 1 mM (Tartoff K. D. and Hobbs C. A., 1987, Improved Media for Growing Plasmid and Cosmid Clones, Bethesda Res. Lab. Focus, 9:12). Cultures have been stopped by centrifugation (8000 rpm, 20 minutes at 10° C.) in an Avanti J-26 XP centrifuge (Beckman Coulter, Brea, USA). Cells have been frozen at −80° C. during at least 2.5 hours and then suspended in 10 mL of Tris HCl buffer (Tris 0.1 M, pH 9). Lysonase™ Bioprocessing Reagent (EMD Millipore) has been used to lysate the cells, according to supplier's recommendation.

Then, cell suspension was centrifuged during 30 minutes at 11000 rpm and at 10° C. The soluble fraction has been collected and submitted to cobalt affinity chromatography using Talon® Metal Affinity resin (Clontech, CA, USA). Protein has been eluted with 100 mM imidazole in 20 mM Tris-HCl, 300 mM NaCl, pH 8.0. Imidazole has been removed from purified extracts after a dialysis step against Tris HCl buffer (Tris 0.1 M, 5 mM CaCl2, pH 7.5 or pH 9 regulated at 45° C.). Purified protein has been quantified using Bio-Rad Bradford protein assay according to manufacturer instructions (Lifescience Bio-Rad, France) and stored at +4° C. The quality of the purification has been assessed on SDS-PAGE after TCA precipitation, the expected protein size being around 29 kDa.

The resulting proteases (i.e., variants of SEQ ID No 1) comprise the amino acid sequence as set forth in SEQ ID No 1, except the specific substitutions as listed in tables 2 and 3 below.

Example 2—Evaluation of the Degrading Activity of the Proteases

The specific degrading activities of wild-type protease and variants thereof have been determined during PLA hydrolysis. 50 mg of a 500 µm PLA powder (PLLA 001—Natureplast) were weighed and introduced in dialysis tubing. The variants have the amino acid sequence as set forth in SEQ ID No 1, except specific substitutions, as listed. The enzymatic sample (1.5 mL of protease preparation containing a fixed concentration of enzyme of 2.5, 5, 10 or 15 mg/L in order to measure the accurate specific activity) was then added in the dialysis tubing before closing it and this latter was introduced in a glass bottle containing 25 mL of 0.1 M Tris-HCl buffer pH 9 or pH 7.5 (regulated at 45° C.). The wild-type protease (SEQ ID No 1) was used as a control.

The depolymerization started by incubating each sample at 45° C. and 170 rpm in a Max Q 4450 incubator (Thermo Fisher Scientific, Inc. Waltham, Mass., USA).

Initial rate of the depolymerization reaction in g of lactic acid and/or dimers of lactic acid generated/g of enzyme/hour was determined by samplings performed at different times during the first 24 hours and analyzed by Ultra High Performance Liquid Chromatography (UHPLC). If necessary, samples were diluted in 0.1 M Tris-HCl buffer pH9 or pH 7.5 (regulated at 45° C.). After filtration on 0.45 µm syringe filter, samples were loaded on UHPLC to monitor the liberation of lactic acid and dimers of lactic acid. Chromatography system used was an Ultimate 3000 UHPLC system (Thermo Fisher Scientific, Inc. Waltham, Mass., USA) including a pump module, an autosampler, a column oven thermostated at 50° C., and a UV detector at 210 nm. The column used was an Aminex HPX-87H (300 mm×7.8 mm), equipped with precolumn, (Supelco, Bellefonte, USA). Lactic acid and dimers of lactic acid were separated using a mobile phase $H_2SO_4$ 5 mM, at a flow rate of 0.5 mL·min$^{-1}$. Injection was 20 µL of sample. Lactic acid and dimers of lactic acid were measured according to standard curves prepared from commercial lactic acid (Sigma-Aldrich L1750-10G) and in house synthetized dimers of lactic acid in the same conditions than samples. The specific degrading activity of PLA hydrolysis (g of equivalent lactic acid (i.e. g of lactic acid and of dimer of lactic acid/hour/g of enzyme) was determined in the linear part of the hydrolysis curve. The results of the different experiments are shown in Table 2 and Table 3 below.

TABLE 2

Specific degrading activity of wild-type protease (SEQ ID no 1) and variants thereof at pH 7.5 (regulated at 45° C.).

| Wild-type protease and Variants thereof | Average Specific degrading activity (g equivalent AL · h$^{-1}$ · g$^{-1}$) ± standard deviation | Improvement factor in degrading activity vs. wild-type activity |
| --- | --- | --- |
| Wild-type protease | 130 ± 27 | 1 |
| V3: T106I | 245 | 1.9 |
| V18: T106L | 342 | 2.6 |
| V6: S101F + S103L | 1045 ± 75 | 8 |
| V13: S101F + S103L + T106I + G131I | 1008 | 7.8 |
| V8: S101F + S103L + T106I | 1844 | 14.2 |
| V19: S101F + S103L + T106L | 1696 | 13 |

These results confirm that proteases of the invention have an increased degrading activity at pH 7.5 as compared to a parent protease of SEQ ID No 1. This is of particular interest for producing biodegradable plastic articles, which incorporate proteases able to degrade one or more polyesters of said plastic articles, since the protease of the invention show great degrading activity under environmental conditions (neutral pH).

Proteases according to V3, V18, V6, V13, V8 or V19, and more particularly according to V8 or V19, would be of particular interest for producing biodegradable PLA-containing plastic articles. Similar tests performed on V1, V2, V4, V5, V7, V9, V10, V11, V12, V14, V15, V16 and V17 at pH 7.5 also confirm that such proteases of the invention have an increased degrading activity at pH 7.5 as compared to a parent protease of SEQ ID No 1 (data not shown).

TABLE 3

Specific degrading activity of the wild-type protease (SEQ ID No 1) and of variants thereof at pH 9.

| Wild-type protease and Variants thereof | Average Specific degrading activity (g equivalent LA · h$^{-1}$ · g$^{-1}$) ± standard deviation | Improvement factor in degrading activity vs. wild-type activity |
| --- | --- | --- |
| Wild-type protease | 520 ± 73 | 1 |
| V1: S101F | 842 | 1.6 |
| V2: S103L | 1044 | 2.0 |
| V3: T106I | 642 ± 48 | 1.2 |
| V4: G131I | 567 ± 13 | 1.1 |
| V5: G133K | 543 ± 60 | 1.05 |
| V6: S101F + S103L | 1100 ± 127 | 2.1 |
| V7: S101F + T106I | 1080 ± 83 | 2.1 |
| V8: S101F + S103L + T106I | 1517 ± 175 | 2.9 |
| V9: T106I + G133K | 799 ± 136 | 1.5 |
| V10: S101F + S103L + G133K | 735 ± 155 | 1.4 |
| V11: S101F + T106I + G133K | 942 ± 125 | 1.8 |
| V12: S101F + S103L + T106I + G133K | 1111 ± 130 | 2.1 |
| V13: S101F + S103L + T106I + G131I | 1525 ± 130 | 2.9 |
| V14: S101L | 824 | 1.6 |
| V15: S101M | 583 | 1.1 |
| V16: S101W | 775 | 1.5 |
| V17: S101Y | 831 | 1.6 |

These results confirm that proteases of the invention may be used in various industrial processes, such as polyester degrading process, wherein a degrading step may be implemented at pH 9. Similar tests performed on V18 and V19 at pH 9 also confirm that such proteases of the invention have an increased degrading activity at pH 9 as compared to a parent protease of SEQ ID No 1 (data not shown).

Example 3—Evaluation of the Activity of Proteases of the Invention

The specific degrading activity of the proteases of the invention has been determined and compared to the specific activity of the wild-type protease of SEQ ID No 1.

Multiple methodologies to assess the specific activity have been used:

(1) Specific activity based upon the pNA hydrolysis;
(2) Specific degrading activity based upon the degradation of a polyester under solid form;
(3) Specific activity based upon the degradation of protein under solid form;
(4) Specific degrading activity based upon the decrease of the turbidity of an emulsion containing PLA;
(5) Specific degrading activity based upon PLA hydrolysis in reactors.

3.1 pNA Hydrolysis

20 µL of protein in solution has been combined to 180µL of 5 mM N-succinyl-Ala-Ala-Ala-p-nitroanilide (pNA) into Tris HCl buffer, 0.1M pH7.5. Enzymatic reaction has been performed at 30° C. under agitation, during at least 15 minutes and absorbance at 405 nm acquired by microplate spectrophotometer (Versamax, Molecular Devices, Sunnyvale, Calif., USA). Specific activity (initial velocity expressed in µmol of released p nitroanilide/min/mg enzyme) has been determined in the linear part of the hydrolysis curve and used to compare activity of the wild type protease with the activity of the variants.

3.2 Degradation of Polyester Under Solid Form

20 µL of enzyme preparation was deposited in a well created in an agarose plate containing PLA. Preparation of agarose plates was realized by solubilizing 450 mg of PLA in 10 mL dichloromethane (DCM) and homogenizing with a vortex. After addition of 90 mL of Tris HCl buffer 0.1 M pH 7-9 followed by a sonication step (Fisher Scientific™ Model 705 Sonic Dismembrator, at 30% of maximum power), DCM has been evaporated at 50° C. The resulting solution has been filtered to remove the undissolved residues. Finally, 12 mL of the 0.5% PLA emulsion was mixed with 3 mL of 1 M Tris HCl buffer pH 9 (regulated at 45° C.) and 15 mL of agarose 2%, to prepare each omnitray (stored at 4° C.).

The diameters of the halos formed due to the polyester degradation by wild-type protease and variants were measured and compared after 4 to 24 hours at 45° C.

3.3 Degradation of Protein Under Solid Form

20 µL of enzyme preparation was deposited in a well created in an agar plate containing milk. Preparation of agar plates was realized by preparing a 28 g/L solution of powdered milk (Regilait™) in water. Then, 15 mL of the milk was mixed with 15 mL of 15 g/L agar, to prepare each omnitray (stored at 4° C.).

The diameters of the halos formed due to the enzymatic milk-protein degradation were measured and compared after 4 to 24 hours at 45° C. Results after 5 hours are shown FIGS. 1A, 1B and 1C and confirm that the wild-type protease (FIG. 1A) and both protease variants V8 (FIG. 1B) and V19 (FIG. 1C) exhibit a protease activity.

3.4 Specific Activity Based Upon the Decrease of the Turbidity of an Emulsion Containing PLA PLA-degrading activity was assayed based on the decrease of turbidity at wavelength of 630 nm at 45° C. for 30 min, and pH 9 with a final concentration of 0.1% (w/v) emulsified PLA in 100 mM Tris-HCl buffer (pH 9 (regulated at 45° C.)), (using an Sonic Dismembrator, at 30% of maximum power). One unit of the PLA-degrading activity was defined as a 1 unit decrease in optical density per min under the assay condition described.

3.5 PLA Hydrolysis in Reactor

A Minibio 500 bioreactors (Applikon Biotechnology B.V., Delft, The Netherlands) was started with 5 g of PLA and 100 mL of 100 mM Tris-HCl buffer pH 7.5 (regulated at 45° C.) containing 2.5 to 10 mg of protease. Agitation was set at 250 rpm using a marine impeller. Bioreactor was thermostated at 45° C. by immersion in an external water bath. pH was regulated at 7.5 by addition of KOH at 3 M. The different parameters (pH, temperature, agitation, addition of base) were monitored thanks to BioXpert software V2.95. 500 µL of reaction medium was sampled regularly.

Amount of LA and dimers of LA were determined by HPLC, as described in example 2.

Specific activity corresponds to specific rate of degradation, and is calculated in mg of total LA and dimers of LA liberated per hour and per mg of enzyme.

Example 4—Evaluation of the Thermostability of the Protease Variants

Different methodologies were used to estimate thermostability:

(1) Residual polyester's depolymerization activity after protein incubation in given conditions of temperatures, times and buffers;
(2) Circular dichroism of proteins in solution;

4.1 Residual Polyester's Degrading Activity

Thermal stabilities of wild type protease and variants were determined by measurement of the residual specific degrading activity (PLA hydrolysis as described in Example 2) recovered after a heat shock. The heat shocks were performed as follow: an enzymatic sample containing a fixed enzyme concentration (0.15 g/L) in 0.1 M Tris-HCl buffer pH 7.5 (regulated at 45° C.), 20 mM of $CaCl_2$, was immersed in a water-bath adjusted at 70° C. during a given time (30 or 60 minutes). The samples were immediately placed on ice after the heat shock. After a step of dilution of the enzyme (up to 0.05 g/L), the specific degrading activities (PLA hydrolysis) recovered after the heat shocked and non-heat shocked samples were measured as detailed in Example 2 (buffer: Tris-HCl 0.1 M pH7.5 (regulated at 45° C.)). The results of residual degrading activities are expressed as a percentage of the specific activity of non-heat shocked sample.

Heat shock conditions and residual degrading activity results after heat shock are showed in Table 4.

TABLE 4

Residual degrading activities of wild-type protease and variant V8 after heat shock.

| Heat shock duration at 70° C. | Wild-type Residual activity (%) | Variant V8 Residual activity (%) |
|---|---|---|
| 30 minutes | 13 | 42 |
| 60 minutes | 2 | 8 |

Table 4 shows that the protease variant V8 retains a greater degrading activity after treatment at 70° C. during 30 to 60 minutes, than wild-type protease.

4.2 Circular Dichroism

Circular dichroism (CD) was performed on a J-815 CD spectrometer (JASCO) to determine and compare the melting temperature ($T_m$) of the protease of SEQ ID No 1 and protease variants of the invention. The $T_m$ corresponds to the temperature at which 50% of the protein is denatured.

Protein sample was prepared at 0.2 mg/mL in buffer containing 100 mM Tris-HCl pH7.5. Experiments were performed in 1 mm optical path quartz cuvette (Starna Scientific Ltd, UK) and far-UV (195-260) CD spectra were first measured to determine two maxima intensities of CD corresponding to the correct folding of the protein.

Thermal denaturation curves of the proteins were obtained by monitoring the change in CD values at 220 nm as the temperature was increased. The rate of temperature increase was 1.5° C. min-1. The temperature of the midpoint of the transition, $T_m$, was calculated by curve fitting of the resultant CD values versus temperature data on the basis of a least-squares analysis using Sigmaplot version 11.0 software.

The $T_m$ obtained reflects the thermostability of the given protein. The higher the $T_m$ is, the more stable the variant is at high temperature.

The Tm of the wild-type protease of SEQ ID No 1 has been evaluated at 49.2+/−0.4° C. without addition of $CaCl_2$. The Tm of the protease variants V8 and V19 have been respectively evaluated at 51.3° C.+/−0.40° C. (+2.10° C.) and 53.4° C.+/−0.30° C. (+4.2° C.), showing respectively a gain of Tm of 2.1° C. and 4.2° C. as compared to the Tm of the esterase of SEQ ID No 1.

The Tm of the wild-type protease of SEQ ID No 1 and of the protease variant V8 have been both evaluated at 70.4+/− 0.2 with an $CaCl_2$) concentration at 5 mM.

Example 5—Biodegradable Polyester Material Containing a Protease of the Invention

5.1 Plastic Compound Preparation Through an Extrusion Process

A plastic compound formulation including a protease variant of the invention was prepared and compared to a plastic compound formulation including a commercial enzyme (Savinase®). Both formulations are listed in Table 5. Percentages are given by weight, based on the total weight of the formulation.

TABLE 5

Plastic compound formulations

|   | PLA | Enzymatic formulation | Protease tested |
|---|-----|----------------------|-----------------|
| A | 90% | 10%                  | Savinase ® 16L  |
| B | 90% | 10%                  | V8              |

Formulation B corresponds to the plastic compound containing the variant of the invention V8 (S101F+S103L+ T106I). Formulation A corresponds to a control containing commercial enzyme (Savinase® 16L, from Novozyme, under solid form, known to degrade PLA; Degradation of Polylactide by commercial proteases; Y. Oda et al. 2000).

In order to compare the results, each enzymatic formulation contains the same amount of pure enzyme (2.1% by weight, based on the total weight of the enzymatic formulation).

The formulations were prepared using:

PLA (polylactic acid polymer, PLA 4043D from NatureWorks), under a powder form (<1 mm) obtained from PLA pellets immersed in liquid nitrogen and micronized using an Ultra Centrifugal Mill ZM 200 system.

Solid Form of Savinase® 16L obtained from commercial liquid form by ultrafiltration on 3.5 kDa membrane, diafiltration, addition of gum Arabic (from Nexira) and dryied by freeze-drying.

Solid form of variant V8 was obtained from fermentation process, followed by purification on cobalt-column, diafiltration, addition of gum arabic and drying by freeze-drying.

Based on these formulations, biodegradable polylactic acid-based plastic compositions have been prepared through an extrusion process. A compounding machine, or co-rotating twin-screw extruder, has been used ("Haake MiniLab II ThermoFisher"). This compounding machine comprised successively a manual feed element, two co-rotating screws and the head of the twin screw.

All powders were mixed together by manual shaking before introduction in the compounding machine. The mix was then introduced in the feeding zone, and push into the screw extruder applying manual pressure. The mix went through co-rotating screws using a rotation speed of the twin-screw of 80 RPM. The temperature of the extrusion was fixed to 165° C. The mix of PLA and protease then arrived in the screw head, comprising one hole of 0.4 mm in diameter, wherein the mix was pushed in order to form strip shapes. This extrudate was then cut with cutting pliers to obtain the plastic composition under granulated form, i.e. a plastic compound.

5.2 Tests of Biodegradability of the Plastic Compositions

The biodegradability of the plastic compounds obtained above has been assessed.

100 mg of each granulated sample A and B were weighted and introduced in dialysis tubing. 3 mL of 0.1 M Tris-HCl buffer pH 8 were added in the dialysis tubing before closing it. The dialysis tubing was then introduced in a plastic bottle containing 50 mL of 0.1 M Tris-HCl buffer pH 8.

The depolymerization was started by incubating each sample at 28° C. or 45° C., 150 rpm in an Infors HT Multitron Pro incubation shaker. Aliquots of 1 mL of buffer were sampled regularly, filtered on 0.22 µm syringe filter, and analyzed by High Pressure Liquid Chromatography (HPLC) with an Aminex HPX-87H column to monitor the liberation of lactic acid (LA) and lactic acid dimer (DP2). Chromatography system used was an Ultimate 3000 UHPLC system (Thermo Fisher Scientific, Inc. Waltham, Mass., USA) including a pump module, an autosampler, a column oven thermostated at 50° C., and an UV detector at 220 nm. Eluent was 5 mM $H_2SO_4$. Injection was 20 µL of sample. Lactic acid and dimers of lactic acid were measured according to standard curves prepared from commercial lactic acid (Sigma-Aldrich L1750-10G) and in house synthetized dimers of lactic acid in the same conditions than samples.

Hydrolysis of plastic articles was calculated based on LA and dimers of LA released. Percentage of degradation was calculated by the molar ratio of LA plus the LA contained in DP2 at a given time versus the LA contained initially in the PLA in the plastic composition. Results of depolymerization, after 10 days of reaction at 28° C. or after 24 hours of reaction at 45° C., are shown in Table 6.

TABLE 6

Depolymerization of plastic compounds including Savinase ® 16L (A) or variant V8 (B), after 10 days of reaction at 28° C. or after 24 hours of reaction at 45° C.

|   | Depolymerization at 28° C. (%) after 10 days | Depolymerization at 45° C. (%) after 24 hours |
|---|---|---|
| A | 7% | 0.3% |
| B | 77% | 75% |

This test confirms the higher degradation rate of the plastic composition B, containing the protease variant V8, compared to the plastic composition A, containing the commercial enzyme. After 10 days, the degradation rate of composition B is 10 time higher than the degradation rate of composition A.

These results interestingly show that variants of the invention have higher PLA-degrading activity and/or higher thermostability as compared to commercial enzymes.

The invention claimed is:

1. A protease which (i) has at least 90% sequence identity to the polypeptide of SEQ ID NO: 1, and (ii) has at least one amino acid substitution selected from S101F/L/M/W/Y, S103L, T106I/L, G131I, and G133K, wherein the positions are numbered by reference to the amino acid sequence set forth in SEQ ID NO: 1, and (iii) exhibits increased polyester degrading activity compared to the polyester degrading activity of the protease of SEQ ID NO: 1.

2. The protease according to claim 1, wherein said protease comprises at least a combination of substitutions selected from S101F/L/M/W/Y+S103L+T106I/L, S101F+S103L, S101F+T106I, T106I+G133K, S101F+S103L+T106I, S101F+S103L+G133K, S101F+T106I+G133K, S101F+S103L+T106L, S101F+S103L+T106I+G133K and S101F+S103L+T106I+G131I.

3. The protease according to claim 1, wherein said protease further comprises at least one amino acid substitution at a position selected from D12, L21, T175, S194, H197, G212, I217 and R247 wherein the positions are numbered by reference to the amino acid sequence set forth in SEQ ID NO: 1.

4. The protease according to claim 1, wherein the protease further comprises at least one amino acid substitution or combination of substitutions selected from D12C+L21C, T175C+R247C, S194P, H197D, G212N, and I217K, wherein the positions are numbered by reference to the amino acid sequence set forth in SEQ ID NO: 1.

5. The protease according to claim 1, wherein said protease exhibits an increased polyester degrading activity compared to the protease of SEQ ID NO: 1 at pH between 7 and 10.

6. The protease according to claim 1, wherein said protease exhibits an increased polyester degrading activity compared to the protease of SEQ ID NO: 1 at pH 7.5 and pH 9.

7. The protease according to claim 1, wherein said protease has at least 95% sequence identity to the polypeptide of SEQ ID NO: 1.

8. The protease according to claim 1, wherein said protease has at least one amino acid substitution selected from S101F/L/M/W/Y, S103L and T106I/L.

9. A composition comprising the protease of claim 1.

10. A plastic compound comprising (i) at least one polyester and (ii) the protease of claim 1.

11. The plastic compound according to claim 10, wherein the protease is able to degrade at least one polyester of the plastic compound.

12. The plastic compound according to claim 10, wherein the polyester comprises polylactic acid.

13. A process for producing a plastic compound comprising mixing a polyester and the protease of claim 1 at a temperature at which the polyester is in a partially or totally molten state.

14. The process according to claim 13, wherein the polyester and the protease are extruded to form a plastic compound.

15. A method of degrading a plastic product containing at least one polyester comprising:
(a) contacting the plastic product with the protease according to claim 1, and
(b) recovering monomers and/or oligomers.

16. The method according to claim 15, wherein the plastic product comprises at least one polyester selected from polylactic acid (PLA), polytrimethylene terephthalate (PTT), polybutylene terephthalate (PBT), polyethylene isosorbide terephthalate (PEIT), polyethylene terephthalate (PET) polyhydroxyalkanoate (PHA), polybutylene succinate (PBS), polybutylene succinate adipate (PBSA), polybutylene adipate terephthalate (PBAT), polyethylene furanoate (PEF), polycaprolactone (PCL), poly(ethylene adipate) (PEA), poly(glycolic acid) (PGA), poly(lactic-co-glycolic acid) (PLGA) and blends/mixtures of these materials.

* * * * *

UNITED STATES PATENT AND TRADEMARK OFFICE
CERTIFICATE OF CORRECTION

PATENT NO. : 11,549,105 B2
APPLICATION NO. : 16/955088
DATED : January 10, 2023
INVENTOR(S) : Alain Marty et al.

Page 1 of 1

It is certified that error appears in the above-identified patent and that said Letters Patent is hereby corrected as shown below:

In the Specification

Column 21,
Line 48, "5'-ACTGTTTCGGCCTGGGTACCATCTCCGGAG-3'" should read
--5'-ACTGTTTCGGCCTGGGTACCATCTCCGGAG-3'--.

Column 25,
Line 26, "to 1804" should read --to 180µL--.

Signed and Sealed this
Fifteenth Day of August, 2023

Katherine Kelly Vidal
*Director of the United States Patent and Trademark Office*

SEQUENCE LISTING

<160> NUMBER OF SEQ ID NOS: 28

<210> SEQ ID NO 1
<211> LENGTH: 276
<212> TYPE: PRT
<213> ORGANISM: Actinomadura sp

<400> SEQUENCE: 1

Ala Thr Gln Asn Asn Pro Pro Ser Trp Gly Leu Asp Arg Ile Asp Gln
1               5                   10                  15

Thr Asn Leu Pro Leu Ser Arg Ser Tyr Thr Tyr Asn Ser Thr Gly Ala
            20                  25                  30

Gly Val Asn Ala Tyr Ile Ile Asp Thr Gly Ile Tyr Thr Ala His Ser
        35                  40                  45

Asp Phe Gly Gly Arg Ala Thr Asn Val Tyr Asp Ala Leu Gly Gly Asn
    50                  55                  60

Gly Gln Asp Cys Asn Gly His Gly Thr His Val Ala Gly Thr Val Gly
65                  70                  75                  80

Gly Ala Ala Tyr Gly Val Ala Lys Ala Val Asn Leu Arg Gly Val Arg
                85                  90                  95

Val Leu Asn Cys Ser Gly Ser Gly Thr Thr Ser Gly Val Ile Ala Gly
            100                 105                 110

Met Asn Trp Val Ala Ser Asn His Val Lys Pro Ala Val Ala Asn Met
        115                 120                 125

Ser Leu Gly Gly Gly Tyr Ser Ser Ser Leu Asn Thr Ala Ala Asn Asn
    130                 135                 140

Leu Ala Ser Ser Gly Val Phe Leu Ala Val Ala Ala Gly Asn Glu Thr
145                 150                 155                 160

Thr Asn Ala Cys Asn Arg Ser Pro Ala Ser Ala Ala Asn Ala Thr Thr
                165                 170                 175

Val Ala Ala Ser Thr Ser Thr Asp Ala Arg Ala Ser Tyr Ser Asn Tyr
            180                 185                 190

Gly Ser Cys Val His Leu Tyr Ala Pro Gly Ser Ser Ile Thr Ser Ala
        195                 200                 205

Trp Leu Asn Gly Gly Thr Asn Thr Ile Ser Gly Thr Ser Met Ala Thr
    210                 215                 220

Pro His Val Ala Gly Thr Ala Ala Leu Tyr Lys Ala Thr Tyr Gly Asp
225                 230                 235                 240

Ala Ser Phe Ser Thr Ile Arg Ser Trp Leu Val Ser Asn Ala Thr Ser
                245                 250                 255

Gly Val Ile Thr Gly Asn Val Ser Gly Thr Pro Asn Leu Leu Leu Asn
            260                 265                 270

Lys Arg Ser Leu
275

<210> SEQ ID NO 2
<211> LENGTH: 81
<212> TYPE: PRT
<213> ORGANISM: artificial sequence
<220> FEATURE:
<223> OTHER INFORMATION: propeptide

<400> SEQUENCE: 2

Ala Pro Ala Val Pro Val Ala Met Ala Ala Gly Gln Gly Val Ala
1               5                   10                  15

Gly Gln Tyr Ile Val Thr Leu Lys Lys Gly Val Ser Val Asp Ser Thr
                20                  25                  30

Val Ala Lys Arg Gly Ile Arg Thr Gln His Arg Phe Gly Lys Val Leu
            35                  40                  45

Asn Gly Phe Ser Ala Lys Leu Thr Asp Asp Gln Leu Ser Lys Leu Arg
    50                  55                  60

Thr Thr Pro Gly Val Ala Ser Ile Glu Gln Asp Ala Val Ile Thr Val
65                  70                  75                  80

Asp

<210> SEQ ID NO 3
<211> LENGTH: 22
<212> TYPE: PRT
<213> ORGANISM: artificial sequence
<220> FEATURE:
<223> OTHER INFORMATION: PelB signal peptide

<400> SEQUENCE: 3

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 4
<211> LENGTH: 357
<212> TYPE: PRT
<213> ORGANISM: Actinomadura sp.

<400> SEQUENCE: 4

Ala Pro Ala Val Pro Val Ala Met Ala Ala Gly Gln Gly Val Ala
1               5                   10                  15

Gly Gln Tyr Ile Val Thr Leu Lys Lys Gly Val Ser Val Asp Ser Thr
                20                  25                  30

Val Ala Lys Arg Gly Ile Arg Thr Gln His Arg Phe Gly Lys Val Leu
            35                  40                  45

Asn Gly Phe Ser Ala Lys Leu Thr Asp Asp Gln Leu Ser Lys Leu Arg
    50                  55                  60

Thr Thr Pro Gly Val Ala Ser Ile Glu Gln Asp Ala Val Ile Thr Val
65                  70                  75                  80

Asp Ala Thr Gln Asn Asn Pro Pro Ser Trp Gly Leu Asp Arg Ile Asp
                85                  90                  95

Gln Thr Asn Leu Pro Leu Ser Arg Ser Tyr Thr Tyr Asn Ser Thr Gly
            100                 105                 110

Ala Gly Val Asn Ala Tyr Ile Ile Asp Thr Gly Ile Tyr Thr Ala His
        115                 120                 125

Ser Asp Phe Gly Gly Arg Ala Thr Asn Val Tyr Asp Ala Leu Gly Gly
    130                 135                 140

Asn Gly Gln Asp Cys Asn Gly His Gly Thr His Val Ala Gly Thr Val

```
            145                 150                 155                 160
        Gly Gly Ala Ala Tyr Gly Val Ala Lys Ala Val Asn Leu Arg Gly Val
                        165                 170                 175

Arg Val Leu Asn Cys Ser Gly Ser Gly Thr Thr Ser Gly Val Ile Ala
                        180                 185                 190

Gly Met Asn Trp Val Ala Ser Asn His Val Lys Pro Ala Val Ala Asn
                        195                 200                 205

Met Ser Leu Gly Gly Gly Tyr Ser Ser Ser Leu Asn Thr Ala Ala Asn
                210                 215                 220

Asn Leu Ala Ser Ser Gly Val Phe Leu Ala Val Ala Ala Gly Asn Glu
        225                 230                 235                 240

Thr Thr Asn Ala Cys Asn Arg Ser Pro Ala Ser Ala Ala Asn Ala Thr
                        245                 250                 255

Thr Val Ala Ala Ser Thr Ser Thr Asp Ala Arg Ala Ser Tyr Ser Asn
                        260                 265                 270

Tyr Gly Ser Cys Val His Leu Tyr Ala Pro Gly Ser Ser Ile Thr Ser
                        275                 280                 285

Ala Trp Leu Asn Gly Gly Thr Asn Thr Ile Ser Gly Thr Ser Met Ala
                        290                 295                 300

Thr Pro His Val Ala Gly Thr Ala Ala Leu Tyr Lys Ala Thr Tyr Gly
        305                 310                 315                 320

Asp Ala Ser Phe Ser Thr Ile Arg Ser Trp Leu Val Ser Asn Ala Thr
                        325                 330                 335

Ser Gly Val Ile Thr Gly Asn Val Ser Gly Thr Pro Asn Leu Leu Leu
                        340                 345                 350

Asn Lys Arg Ser Leu
                        355

<210> SEQ ID NO 5
<211> LENGTH: 1071
<212> TYPE: DNA
<213> ORGANISM: artificial sequnce
<220> FEATURE:
<223> OTHER INFORMATION: gene encoding non-matured protease

<400> SEQUENCE: 5 gccccgctg tccccgtcgc catggccgct gccggccagg gtgtcgccgg ccagtacatc          60
gttactctga agagggcgt gtctgttgac tctaccgttg ctaagcgagg catccgaacc         120
cagcaccgat tcggaaaggt cctgaacgga ttttccgcca agctcaccga cgatcagctg        180
tctaagctcc gaaccactcc cggcgtcgcc tctatcgagc aggacgctgt tattaccgtc        240
gatgccactc agaacaaccc tccctcctgg ggtctcgacc gaatcgacca gaccaacctg        300
cctctctctc gatcgtacac ctacaactct actggagccg cgtcaacgc ttacatcatt         360 gacaccggaa tttacactgc ccactccgat ttcggcggtc gagctaccaa cgtgtacgac        420
gccctgggag caacggtca ggattgcaac ggtcacggaa cccatgtggc cggcactgtt         480
ggtggagccg cttacggtgt cgccaaggct gtgaacctgc gaggtgtccg agtgctcaac        540
tgttccggct ctggtaccac ttccggagtc atcgctggca tgaactgggt ggcctctaac        600
catgttaagc ccgccgtcgc taacatgtcc ctgggcggtg atactcctc ttcgctgaac         660 accgccgcta acaacctcgc ttcctctgga gtgttcctgg ccgttgccgc tggcaacgag        720
accactaacg cctgcaaccg atcgcctgct tccgccgcta acgctaccac tgtggccgct        780
tcgacctcta ctgacgcccg agcttcttac tcgaactacg gttcttgtgt tcacctctac        840
```

```
gctcccggat cgtccatcac ctctgcctgg ctgaacggcg gtaccaacac tatttctggc      900
acctcgatgg ccactcctca tgttgctggt accgccgctc tctacaaggc cacttacgga      960
gacgcttcct tttctaccat tcgatcctgg ctggtgtcta acgccacctc gggtgtcatc     1020
actggtaacg tctctggaac tcccaacctg ctcctgaaca agcgaagcct g              1071
```

```
<210> SEQ ID NO 6
<211> LENGTH: 8
<212> TYPE: PRT
<213> ORGANISM: artificial sequence
<220> FEATURE:
<223> OTHER INFORMATION: 6xhistidine tag

<400> SEQUENCE: 6

Leu Glu His His His His His His
1               5

<210> SEQ ID NO 7
<211> LENGTH: 36
<212> TYPE: DNA
<213> ORGANISM: artificial sequence
<220> FEATURE:
<223> OTHER INFORMATION: PAM S101F forward

<400> SEQUENCE: 7
gtccgagtgc tcaactgttt cggctctggt accact                                 36

<210> SEQ ID NO 8
<211> LENGTH: 36
<212> TYPE: DNA
<213> ORGANISM: artificial sequence
<220> FEATURE:
<223> OTHER INFORMATION: PAM S101L forward

<400> SEQUENCE: 8
gtccgagtgc tcaactgtct gggctctggt accact                                 36

<210> SEQ ID NO 9
<211> LENGTH: 36
<212> TYPE: DNA
<213> ORGANISM: artificial sequence
<220> FEATURE:
<223> OTHER INFORMATION: PAM S101M forward

<400> SEQUENCE: 9
gtccgagtgc tcaactgtat gggctctggt accact                                 36

<210> SEQ ID NO 10
<211> LENGTH: 36
<212> TYPE: DNA
<213> ORGANISM: artificial sequence
<220> FEATURE:
<223> OTHER INFORMATION: PAM S101W forward

<400> SEQUENCE: 10
gtccgagtgc tcaactgttg gggctctggt accact                                 36

<210> SEQ ID NO 11
<211> LENGTH: 36
<212> TYPE: DNA
<213> ORGANISM: artificial sequence
<220> FEATURE:
<223> OTHER INFORMATION: PAM S101Y forward

<400> SEQUENCE: 11
```
gtccgagtgc tcaactgtta cggctctggt accact                                    36

<210> SEQ ID NO 12
<211> LENGTH: 36
<212> TYPE: DNA
<213> ORGANISM: artificial sequence
<220> FEATURE:
<223> OTHER INFORMATION: PAM S101 reverse

<400> SEQUENCE: 12
acagttgagc actcggacac ctcgcaggtt cacagc                                    36

<210> SEQ ID NO 13
<211> LENGTH: 35
<212> TYPE: DNA
<213> ORGANISM: artificial sequence
<220> FEATURE:
<223> OTHER INFORMATION: PAM S103L forward

<400> SEQUENCE: 13
tgctcaactg ttccggcctg ggtaccactt ccgga                                     35

<210> SEQ ID NO 14
<211> LENGTH: 33
<212> TYPE: DNA
<213> ORGANISM: artificial sequence
<220> FEATURE:
<223> OTHER INFORMATION: PAM S103 reverse

<400> SEQUENCE: 14
gccggaacag ttgagcactc ggacacctcg cag                                       33

<210> SEQ ID NO 15
<211> LENGTH: 35
<212> TYPE: DNA
<213> ORGANISM: artificial sequence
<220> FEATURE:
<223> OTHER INFORMATION: PAM T106I forward

<400> SEQUENCE: 15
gttccggctc tggtaccatc tccggagtca tcgct                                     35

<210> SEQ ID NO 16
<211> LENGTH: 35
<212> TYPE: DNA
<213> ORGANISM: artificial sequence
<220> FEATURE:
<223> OTHER INFORMATION: PAM T106L forward

<400> SEQUENCE: 16
gttccggctc tggtaccctg tccggagtca tcgct                                     35

<210> SEQ ID NO 17
<211> LENGTH: 36
<212> TYPE: DNA
<213> ORGANISM: artificial sequence
<220> FEATURE:
<223> OTHER INFORMATION: PAM T106 reverse

<400> SEQUENCE: 17
ggtaccagag ccggaacagt tgagcactcg gacacc                                    36

<210> SEQ ID NO 18
<211> LENGTH: 34
<212> TYPE: DNA
<213> ORGANISM: artificial sequence

```
<220> FEATURE:
<223> OTHER INFORMATION: PAM G131I forward

<400> SEQUENCE: 18
cgctaacatg tccctgatcg gtggatactc ctct                                34

<210> SEQ ID NO 19
<211> LENGTH: 33
<212> TYPE: DNA
<213> ORGANISM: artificial sequence
<220> FEATURE:
<223> OTHER INFORMATION: PAM G131 reverse

<400> SEQUENCE: 19
cagggacatg ttagcgacgg cgggcttaac atg                                 33

<210> SEQ ID NO 20
<211> LENGTH: 36
<212> TYPE: DNA
<213> ORGANISM: artificial sequence
<220> FEATURE:
<223> OTHER INFORMATION: PAM G133K forward

<400> SEQUENCE: 20
ctaacatgtc cctgggcggt aagtactcct cttcgc                              36

<210> SEQ ID NO 21
<211> LENGTH: 33
<212> TYPE: DNA
<213> ORGANISM: artificial sequence
<220> FEATURE:
<223> OTHER INFORMATION: PAM G133 reverse

<400> SEQUENCE: 21
gcccagggac atgttagcga cggcgggctt aac                                 33

<210> SEQ ID NO 22
<211> LENGTH: 27
<212> TYPE: DNA
<213> ORGANISM: artificial sequence
<220> FEATURE:
<223> OTHER INFORMATION: PAM_S101F_S103L

<400> SEQUENCE: 22
gagtgctcaa ctgtttcggc ctgggta                                        27

<210> SEQ ID NO 23
<211> LENGTH: 27
<212> TYPE: DNA
<213> ORGANISM: artificial sequence
<220> FEATURE:
<223> OTHER INFORMATION: PAM_S101F_S103L reverse

<400> SEQUENCE: 23
tcggaagtgg tacccaggcc gaaacag                                        27

<210> SEQ ID NO 24
<211> LENGTH: 30
<212> TYPE: DNA
<213> ORGANISM: artificial sequence
<220> FEATURE:
<223> OTHER INFORMATION: PAM_S101F_S103L_T106I forward

<400> SEQUENCE: 24
actgtttcgg cctgggtacc atctccggag                                     30
```

```
<210> SEQ ID NO 25
<211> LENGTH: 31
<212> TYPE: DNA
<213> ORGANISM: artificial sequence
<220> FEATURE:
<223> OTHER INFORMATION: PAM_S101F_S103L_T106I reverse

<400> SEQUENCE: 25
ggagatggta cccaggccga aacagttgag c                              31

<210> SEQ ID NO 26
<211> LENGTH: 22
<212> TYPE: DNA
<213> ORGANISM: artificial sequence
<220> FEATURE:
<223> OTHER INFORMATION: PAM_T106L bis forward

<400> SEQUENCE: 26
ggtaccctgt ccggagtcat cg                                        22

<210> SEQ ID NO 27
<211> LENGTH: 20
<212> TYPE: DNA
<213> ORGANISM: artificial sequence
<220> FEATURE:
<223> OTHER INFORMATION: PAM_S103L_T106L  reverse

<400> SEQUENCE: 27
tccggacagg gtacccaggc                                           20

<210> SEQ ID NO 28
<211> LENGTH: 386
<212> TYPE: PRT
<213> ORGANISM: artificial sequence
<220> FEATURE:
<223> OTHER INFORMATION: protease

<400> SEQUENCE: 28
```

Met Arg Arg Arg Thr Leu Pro Ile Ala Val Leu Ala Ala Val Pro Leu
1               5                   10                  15

Ala Met Ala Gly Ala Leu Pro Ala Gly Ala Ala Pro Ala Ala Pro Ala
            20                  25                  30

Val Pro Val Ala Met Ala Ala Ala Gly Gln Gly Val Thr Gly Gln Tyr
        35                  40                  45

Ile Val Thr Leu Lys Lys Gly Val Ser Val Asp Ser Thr Val Ser Lys
    50                  55                  60

Arg Gly Ile Arg Thr Gln Tyr Arg Phe Gly Lys Val Leu Asn Gly Phe
65                  70                  75                  80

Ser Ala Lys Leu Thr Asp Ala Gln Leu Ala Lys Leu Arg Thr Thr Pro
                85                  90                  95

Gly Val Ala Ser Ile Glu Gln Asp Ala Val Ile Lys Ala Asp Ala Thr
            100                 105                 110

Gln Thr Asn Pro Pro Ser Trp Gly Ile Asp Arg Ile Asp Gln Thr Asn
        115                 120                 125

Leu Pro Leu Ser Asn Ser Tyr Thr Tyr Asn Ser Thr Gly Ala Gly Val
    130                 135                 140

Asn Ala Tyr Ile Ile Asp Thr Gly Ile Tyr Thr Ala His Pro Asn Phe
145                 150                 155                 160

Gly Gly Arg Ala Thr Asn Val Tyr Asp Ala Leu Gly Gly Asn Gly Gln
                165                 170                 175

```
Asp Cys Asn Gly His Gly Thr His Val Ala Gly Thr Val Gly Ser Thr
            180             185                 190

Ser Tyr Gly Val Ala Lys Ser Val Asn Leu Arg Gly Val Arg Val Leu
        195                 200                 205

Asn Cys Ser Gly Ser Gly Thr Thr Ser Gly Val Ile Ala Gly Met Asn
        210             215                 220

Trp Val Ala Gly Asn His Val Lys Pro Ala Val Ala Asn Met Ser Leu
225                 230                 235                 240

Gly Gly Gly Tyr Ser Ser Ser Ile Asn Thr Ala Ala Asn Asn Leu Ala
                245             250                 255

Asn Ala Gly Val Phe Leu Ala Ala Ala Ala Gly Asn Glu Asn Thr Asn
                260             265                 270

Ala Cys Asn Arg Ser Pro Ala Ser Ala Ala Asn Ala Thr Thr Val Ala
        275             280                 285

Ala Ser Thr Ser Thr Asp Ala Arg Ala Ser Tyr Ser Asn Tyr Gly Ser
        290             295             300

Cys Val His Leu Tyr Ala Pro Gly Ser Ser Ile Thr Ser Thr Trp Leu
305                 310             315             320

Asn Gly Gly Thr Asn Thr Ile Ser Gly Thr Ser Met Ala Thr Pro His
            325             330             335

Val Ala Gly Val Ala Ala Leu Tyr Lys Ala Thr Tyr Gly Asp Ala Ser
            340             345             350

Phe Ser Thr Ile Arg Ser Trp Leu Thr Ser Asn Ala Thr Ser Gly Val
        355             360             365

Ile Thr Gly Asn Pro Ser Gly Thr Pro Asn Arg Leu Leu Asn Lys Arg
    370             375             380

Ser Leu
385
```